US007846450B2

(12) United States Patent
Figdor et al.

(10) Patent No.: US 7,846,450 B2
(45) Date of Patent: Dec. 7, 2010

(54) MELANOMA ASSOCIATED PEPTIDE ANALOGUES AND VACCINES AGAINST MELANOMA

(75) Inventors: Carl Gustav Figdor, Hertogenbosch (NL); Gosse Jan Adema, Groesbeek (NL)

(73) Assignee: United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 12/337,834

(22) Filed: Dec. 18, 2008

(65) Prior Publication Data

US 2009/0232839 A1 Sep. 17, 2009

Related U.S. Application Data

(60) Division of application No. 10/808,681, filed on Mar. 25, 2004, now abandoned, which is a continuation of application No. 09/214,836, filed as application No. PCT/EP97/03712 on Jul. 8, 1997, now abandoned.

(30) Foreign Application Priority Data

Jul. 11, 1996 (EP) .................................. 96201945

(51) Int. Cl.
*A61K 39/00* (2006.01)

(52) U.S. Cl. ..................... 424/185.1; 530/328; 514/15

(58) Field of Classification Search .............. 424/185.1; 530/328; 514/15
See application file for complete search history.

(56) References Cited

U.S. PATENT DOCUMENTS

| | | |
|---|---|---|
| 4,405,712 A | 9/1983 | Vande Woude et al. |
| 4,485,086 A | 11/1984 | Wong |
| 4,497,796 A | 2/1985 | Salser et al. |
| 4,727,028 A | 2/1988 | Santerre et al. |
| 4,740,463 A | 4/1988 | Weinberg et al. |
| 5,190,931 A | 3/1993 | Inouye |
| 5,208,149 A | 5/1993 | Inouye |
| 5,262,177 A | 11/1993 | Brown et al. |
| 5,342,774 A | 8/1994 | Boon et al. |
| 5,376,531 A | 12/1994 | Anderson et al. |
| 5,518,913 A | 5/1996 | Massie et al. |
| 5,639,860 A | 6/1997 | Tanaka et al. |
| 5,643,873 A | 7/1997 | Barrett et al. |
| 5,648,458 A | 7/1997 | Cwirla et al. |
| 5,728,802 A | 3/1998 | Barrett et al. |
| 5,731,172 A | 3/1998 | Saito et al. |
| 5,783,567 A | 7/1998 | Hedley et al. |
| 5,837,511 A | 11/1998 | Falck-Pedersen et al. |
| 5,844,075 A | 12/1998 | Kawakami et al. |
| 5,874,560 A | 2/1999 | Kawakami et al. |
| 5,891,432 A | 4/1999 | Hoo |
| 5,965,381 A | 10/1999 | van der Bruggen et al. |
| 5,965,535 A | 10/1999 | Chaux et al. |
| 5,994,106 A | 11/1999 | Kovesdi et al. |
| 5,994,128 A | 11/1999 | Fallaux et al. |
| 5,994,523 A | 11/1999 | Kawakami et al. |
| 6,033,908 A | 3/2000 | Bout et al. |
| 6,040,174 A | 3/2000 | Imler et al. |
| 6,194,195 B1 | 2/2001 | Tanaka et al. |
| 6,204,052 B1 | 3/2001 | Bout et al. |
| 6,245,525 B1 | 6/2001 | Martelange et al. |
| 6,270,778 B1 | 8/2001 | Kawakami et al. |
| 6,291,430 B1 | 9/2001 | Chaux et al. |
| 6,303,756 B1 | 10/2001 | Martelange et al. |
| 6,369,211 B1 | 4/2002 | Chaux et al. |
| 6,407,063 B1 | 6/2002 | Luiten et al. |
| 6,426,217 B1 | 7/2002 | Chaux et al. |
| 6,500,919 B1 | 12/2002 | Adema et al. |
| 6,537,560 B1 | 3/2003 | Kawakami et al. |
| 2002/0076392 A1 | 6/2002 | Hoo |
| 2003/0096787 A1 | 5/2003 | Perricaudet et al. |
| 2003/0144482 A1 | 7/2003 | Kawakami et al. |

FOREIGN PATENT DOCUMENTS

| | | |
|---|---|---|
| CA | 2 053 187 | 4/1993 |
| CA | 2053187 | 4/1993 |
| EP | 0174608 | 3/1986 |
| EP | 0 668 350 A | 8/1995 |
| FR | 2 707 664 | 1/1995 |

(Continued)

OTHER PUBLICATIONS

Adema et al., Melanocyte lineage-specific antigens recognized by monoclonal antibodies NKI-beteb, HMB-50, and HMB-45 are encoded by a single cDNA, The American Journal of Pathology, 1993, vol. 143, No. 6, pp. 1579-1585.

(Continued)

*Primary Examiner*—Stephen L Rawlings
(74) *Attorney, Agent, or Firm*—Leydig, Voit & Mayer

(57) ABSTRACT

The present invention is concerned with cancer treatment and diagnosis, especially with melanoma associated peptide analogues with improved immunogenicity, epitopes thereof, vaccines against melanoma, tumor infiltrating T lymphocytes recognizing the antigen and diagnostics for the detection of melanoma and for the monitoring of vaccination. The peptides according to the invention can be exploited to elicit native epitope-reactive Cm. Usage of the peptides with improved immunogenicity may contribute to the development of CTL-epitope based vaccines in viral disease and cancer.

3 Claims, 5 Drawing Sheets

FOREIGN PATENT DOCUMENTS

| FR | 2 707 664 | 11/1995 |
|---|---|---|
| JP | 9027482 A2 | 1/1997 |
| WO | WO 92/21767 | 12/1992 |
| WO | WO 93/14189 | 4/1993 |
| WO | WO 94/23067 | 10/1994 |
| WO | WO 94/28152 | 12/1994 |
| WO | WO 95/02697 | 1/1995 |
| WO | WO 95/22561 | 8/1995 |
| WO | WO 95/29193 | 11/1995 |
| WO | WO 98/02538 | 1/1998 |
| WO | WO 98/31398 | 7/1998 |
| WO | WO 99/06544 | 2/1999 |
| WO | WO 99/14326 | 3/1999 |
| WO | WO 99/45098 | 9/1999 |
| WO | WO 99/53061 | 10/1999 |
| WO | WO 00/20445 | 4/2000 |
| WO | WO 00/20581 | 4/2000 |

OTHER PUBLICATIONS

Adema, et al., Molecular Characterization of the Melanocyte Lineage-specific Antigen gp100, J. Biol. Chem., 1994, vol. 269, No. 31, pp. 20126-20133.
Arceci, RJ., The potential for antitumor vaccination in acute myelogenous leukemia, Journal of Molecular Medicine, 1998, pp. 80-93, vol. 76.
Bakker et al., Int J. Cancer, Jan. 27, 1997, pp. 302-309, vol. 70 (3).
Bodey et al., Failure of cancer vaccines: the significant limitations of this approach to immunotherapy, Anticancer Research, 2000, pp. 2665-2676, vol. 20.
Boon, T., Toward a genetic analysis of tumor rejection antigens, Advances in Cancer Research, 1992, pp. 177-210, vol. 58.
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. Cell Biol., 1990, 11:2129-2138.
Cox et al., Identification of a peptide recognized by five melanoma-specific human cytotoxic T cell lines, Science, 1994, pp. 716-719, vol. 264.
Curti, Crit. Rev. Oncol/Hematol. 14:29-39, 1993.
De Vries et al., Heterogeneous expression of immunotherapy candidate proteins gp100, MART-1, and tyrosinase in human melanoma cell lines and inhuman melanocytic lesions, Cancer Research, 1997, pp. 3223-3229, vol. 57, No. 15.
Ezzell, C., Cancer "vaccines": an idea whose time has come?, Journal of NIH Research, pp. 46-49, vol. 7, 1995.
Gao et al., Tumor vaccination that enhances antitumor T-cell responses does not inhibit th growth of established tumor, Journal of Immunotherapy, 2000, pp. 643-653, vol. 23, No. 6.
Gura, T., Systems for identifying drugs are often faulty, Science, 1997, pp. 1041-1042, vol. 278.
Hu et al., Enhancement of cytolytic T lymphocyte precursor frequence in melanoma patients following immunization with MAGE-1 peptide, Cancer Research, 1996, pp. 2479-2483, vol. 56.
Jaeger et al, Generation of cytotoxic T-cell responses with synthetic melanoma-associated peptides in vivo, International Journal of Cancer, 1996, pp. 162-169, vol. 66, No. 2.
Kristensen et al., Evidence that the newly cloned low-density-lipoprotein receptor related protein (LRP) is the alpha 2-macroglobulin receptor, Febs Letters, Dec. 1990, pp. 151-155, vol. 256, No. 1,2.
Lee et al., Increased vaccine-specific T cell frequency after peptide-based vaccination correlates with increased susceptibility to in vitro stimulation but does not lead to tumor regression, Journal of Immunology, 1999, pp. 6292-6300, vol. 163.
Mukherji et al., Induction of antigen-specific cytolytic T cells in situ in human melanoma by immunization, proceedings of the National Academy of Science, 1995, pp. 8078-8082, vol. 92.

Gillies et al., Antigen binding and biological activities of engineered mutant chimeric antibodies with human tumor specificities, Human Antibody. Hybridomas, 1990, vol. 1, No. 1, pp. 47-54.
Jain, Sci Am. 271:58-65,1994.
Kawakami, et al., Identification of a human melanoma antigen recognized by tumor-infiltrating lymphocytes associated with in vivo tumor rejection, Proc. Natl. Acad. Sci., 1994, vol. 91, pp. 6458-6462.
Kwon et al., A melanocyte-specific gene, Pmel 17, maps near the silver coat color locus on mouse chromosome 10 and is in a cyntenic region on human chromosome 12, Proceedings of the National Academy of Sciences of USA, 88:20;9228-9232, Oct. 15, 1991, Washington, D.C., USA.
Lazar et al., Transforming Growth Factor a: Mutation of Aspartic Acid 47 and Leucine 48 Results in Different Biological Activities, Mol. Cell Biol., 1988, vol. 8, pp. 1247-1252.
Osband et al., Problems in the investigational study and clinical use of cancer immunotherapy, Immunology Today, 1990, 11(6):193-195.
Rivoltini et al., Binding and Presentation of Peptides Derived from Melanoma Antigens MART-1 and Glycoprotein-100 by HLA-A2 Subtypes, Journal of Immunology, May 1996, pp. 3882-3891.
Marchand et al., Tumor regression responses in melanoma patients treated with a peptide encoded by gene MAGE-3, Int. J. Cancer, 1995 63, 883-885, Wiley-Liss, Inc.
Rosenberg et al., Immunologic and therapeutic evaluation of a synthetic peptide vaccine for the treatment of patients with metastatic melanoma, Nature Medicine, Mar. 1998, vol. 4, No. 3, pp. 321-327.
Rosenberg et al., Cancer vaccines based on the identitcation of genes encoding cancer regression antigens, Immunology Today, vol. 18, No. 4, Apr. 1997, pp. 175-182.
Salgaller et al., Immunization against Epitopes in the Human Melanoma Antigen gp100 following Patient Immunization with Synthetic Peptides, Cancer Research, Oct. 1996, pp. 4749-4757, vol. 56.
Sinkovics et al., Vaccination against human cancers (review), International Journal of Cancer, 2000, pp. 81-96, vol. 16.
Slingluff et al., Melanomas with concordant loss of multiple differentiation proteins: immune escape that may be overcome by targeting unique or undefined antigens, Cancer Immunology & Immunotherapy. 2000, pp. 661-672, vol. 48, No. 12.
Slingluff et al., Recognition of Human Melanoma Cells by HLA-A2.1-Restricted Cytotoxic T Lymphocytes Is Mediated by at Least Six Shared Peptide Epitopes, The Journal of Immunology, Apr. 1,1993, pp. 2955-2963, vol. 150, No. 7, The American Association of Immunologists, USA.
Splitler, LE, Cancer vaccines: the interferon analogy, Cancer Biotherapy, 1995, pp. 1-3, vol. 10, No. 1.
Tao et al, Studies of Aglycosylated Chimeric Mouse-Human IgG, J. Immunol., 1989, vol. 143, No. 8, pp. 2595-2601.
Timmerman et al., Dendritic cell vaccines for cancer immunotherapy, Annual Review of Medicine, 1999, pp. 407=29, vol. 50.
Vogel et al., Human 95kD melanocyte-specific secreted glycoprotein mRNA, 3' end EMBL Database, Accession No. M32295, Nov. 26, 1990.
Yamshchikov et al., Analysis of a natural immune response against tumor antigens in a melanoma survivor: Lessons applicable to clinical trial evaluations, Clinical Cancer Research, pp. 909s-916s, vol. 7, No. 3 supplement, 2001.
Zaks et al., Immunization with a peptide epitope (p369-377) from HER-2/neu leads to peptide-specific cytotoxic T lymphocytes that fail to recognize HER-2/neu+ tumors, Cancer Research, pp. 4902-4908, vol. 58, 1998.
Bocchia et al., Abstract, Specific binding of leukemia oncogene fusion protein peptides to H class I molecules, Blood, May 15, 1995, pp. 2680-2684, vol. 85; No. 10.
Bristow et al., Abstract, Solid-phase antigen binding by purified immunoproteins from antigen-specific monoclonal T cell hybridomas, Mol. Immunol. Jul. 1989, pp. 611-624, vol. 26, No. 7.
Gether et al., Abstract, Stable expression of high affinity NK1 (substance P) and NK2 (neurokinin A) receptors but low affinity NK3 (neurokinin B) receptors in transfected CHO cells, FEBS Letters, Jan. 27, 1992, pp. 241-244, vol. 296, No. 3.
Hartwell et al., Integrating Genetic Approaches into the Discovery of Anticancer Drugs, Science, Nov. 7, 1997, pp. 1064-1068, vol. 278.

Lilly et al., Abstract, Effects of chronic airway inflammation on the activity and enzyme inactivation of neuropeptides in guinea pig lungs, J. Clin. Invest, Jun. 1994, pp. 2667-2674, vol. 93, No. 6.

Phan et al., Cancer regression and autoimmunity induced by cytotoxic T lymphocyte-associated antigen 4 blockade in patients with metastatic melanoma, PNAS, Jul. 8, 2003, pp. 8372-8377, vol. 100, No. 14.

Rosenberg et al., Impact of Cytokine Administration on the Generation of Antitumor Reactivity in Patients with Metastatic Melanoma Receiving a Peptide Vaccine, 1999, The Journal of Immunology, pp. 1690-1695.

Rosenberg, Steven A., Progress in human tumour immunology and immunotherapy, Nature, May 17, 2001, pp. 380-384, vol. 411.

Adema et al., Melanocyte Lineage-Specific Antigens Recognized by Monoclonal Antibodies NKI-beteb, HMB-50, and HMB-45 are Encoded by a Single cDNA, American Journal of Pathology, Dec. 1993, pp. 1579-1585, vol. 143, No. 6.

Kwon et al, a melamocyte-specific gene, Pmel 17, maps near the silver coat color locus on mouse chromosome 10 and is in a syntenic region on human chromosome 12, Proc. Natl. Acad. Sci, Oct. 1991, pp. 9228-9232, vol. 88, USA.

Adema et al., T Cell Stimulatory Tumor Antigens, Keystone Symposium; 1993, J. Cell Biochem, supplement 17, part D, p. 107.

Shilyansky at al., T-cell receptor usage by melanoma-specific clonal and highly oligoclonal tumor-infiltrating lymphocyte lines, Proc. Natl. Acad. Sci., Mar. 1994, pp. 2829-2833, vol. 91.

Storkus et al., Identification of Human Melanoma Peptides Recognized by Class I Restricted Tumor Infiltrating T Lymphocytes, The Journal of Immunology, Oct. 1, 1993, pp. 3719-3727, vol. 151, No. 7, USA.

O'Neil et al., Detection of Shared MHC-Restricted Human Melanoma Antigens after Vaccinia Virus-Mediated Transduction of Genes Coding for HLA, Aug. 1, 1993, pp, 1410-1418, vol. 151, USA.

Kawakami et al., T-Cell Recognition of Human Melanoma Antigens, Journal of Immunotherapy, 1993, pp. 88-93, vol. 14, Raven Press, Ltd., New York.

Miles et al., HiTech . . . Multiple Peptide Synthesis (Pepscan Method) for the Systematic Analysis of B- and T-cell Epitopes: Application to Parasite Proteins, Parasitology Today, 1989, vol. 5, No. 12.

Arnholdt et al., Analysis and Partial Epitope Mapping of Human T Cell Responses to *Trypanosoma cruzi* Cysteinyl Proteinase, The Journal of Immunology, Sep. 15, 1993. pp. 3171-3179, vol. 151, No. 6, USA.

Reynolds et al., T and B Cell Epitope Mapping of SM23, an Integral Membrane Protein of *Schistosoma mansoni*, The Journal of Immunology, Dec. 15, 1992, pp. 3995-4001, vol. 149, No. 12, USA.

Kawakami et al., Identification of a human melanoma antigen recognized by tumor-infiltrating lymphocytes associated with in vivo tumor rejection, Proc. Natl. Acad. Sci, Jul. 1994, pp. 6458-6462, vol. 91, USA.

Bakker et al., Melanocyte Lineage-specific Antigen gp100 Is Recognized by Melanoma-derived Tumor-infiltrating Lymphocytes, The Journal of Experimental Medicine, Mar. 1994, pp. 1005-1009, vol. 179.

Hunt et al., Characterization of Peptides Bound to the Class I MHC Molecule HLA-A2.1 by Mass Spectrometry, Science, pp. 1261-1263, vol. 255, 1992.

Slingluff et al., Recognition of Human Melanoma Cells by HLA-A2. 1-Restricted Cytotoxic T Lymphocytes Is Mediated by at Least Six Shared Peptide Epitopes, The Journal of Immunology, Apr. 1993, pp. 2955-2963, vol. 150, No. 7, USA.

Adema et al., Molecular Characterization of the Melanocyte Lineage-specific Antigen gp100, Aug. 5, 1994, pp. 20126-20133, vol. 269, No. 31, USA.

Kawakami et al., Recognition of Multiple Epitopes in the Human Melanoma Antigen gp100 by Tumor-Infiltrating T Lymphocytes Associated with In Vivo Tumor Regression, The Journal of Immunology, 1995, pp. 3961-3968, vol. 154.

Traversari, C., et al., "A Nonapeptide Encoded by Human Gene MAGE-1 Is Recognized on HLA-A1 by Cytolytic T Lymphocytes Directed against Tumor Antigen MZ2-E", *J. Exp. Med.*, vol. 176, 1453-1457 (Nov. 1992).

Altschul, S.F. et al. (1990) J. Mol. Biol. 215, pp. 403-410.
Anderson et al. (2000) Tissue Antigens 55(6), pp. 519-531.
Anichini, A., et al., (1993), J. Exp. Med. 177, pp. 989-998.
Baker, S.J. et al. (1990), Science 249, pp. 912-915.
Bean, M.A. et al. (1975) Cancer Res. 35, pp. 2902-2907.
Bowie et al., (1990), Science, 257, pp. 1306-1310.
Brichard et al. (1993) J. Exp. Med. 178, pp. 489-495.
Chirgwin, J.M. et al. (1979) Biochemistry 18, pp. 5294-5299.
Cleveland, D.W. et al. (1977) J. Biol. Chem. 253, pp. 1102-1106.
Cox, A.L. et al. (1994) Science 264, pp. 716.
Dadaglio, G. et al. (1991) J. Immunol. 147, pp. 2302.
Devereux, J. et al. (1984) Nucleic Acids Res. 12, pp. 387.
Eisinger, M. et al. (1982) Proc. Nat'l. Acad. Sci. USA 79, pp. 2018-2022.
Espevik and Nissen-Meyer (1986) J. lmmunol. Meth. 95, pp. 99.
Esclamado, R.M. et al. (1986) Am. J. Surg. 152, pp. 376-385.
Falk, K. et al. (1991) Nature 351, pp. 290.
Felgner, P.L. et al. (1987) Proc. Nat'l. Acad. Sci. USA 84, pp. 7413-7417.
Feltkamp et al. (1994) Mol. Immunol. 31(18), pp. 1391-1401.
Fisher, B. et al. (1989), J. Clin. Oncol. 7, pp. 250-261.
Gotch, F. et al. (1987) Nature 326, pp. 881.
Graham, F.L. et al. (1973), Virology 52, pp. 456.
Green, M.R. (1991) Ann. Rev, Cell Biol. 7, pp. 559-599.
Guichard et al. (2000) J. Med Chem. 43, pp. 3803-3808.
Haisma, H.J. et al. (1986) J. Nucl. Med. 27, pp. 1890.
Hall, R. et al. (1984) Nature 311, pp. 379-387.
Hnatowich, D.J. et al. (1983) J. Immunol. Meth. 65, pp. 147-157.
Holmes (2001) Expert Opinion on Investigational Drugs, pp. 511-519.
Jones, P.T. et al. (1986) Nature 321, pp. 522-525.
Katano, M. et al. (1984) J. Cancer Res. Clin. Oncol. 108, pp. 197.
Kim, R.Y. et al. (1992) Exp. Eye Res. 55, pp. 657-662.
Kohler, G. et al. (1975) Nature 256; pp. 495-497.
Knuth, A. et al. (1192) Cancer Surveys pp. 39-52.
Kozak, M. (1987) Nucleic Acids Res. 15, pp. 8125-8148.
Ksander, B.R. et al. (1991) Investigative Ophtamology & Visual Science, 32, pp. 3198-3208.
Kwon, B.S. et al. (1987) Mol. Biol. Med. 4, pp. 339-355.
Kyte, J. et al. (1982) J. Mol. Biol. 157, pp. 105-132.
Lenstra, J.A. et al. (1990), Arch. Virol. 110, pp. 1-24.
Loenen, W.A.M. et al. (1991) Eur. J. Immunol. 22, pp. 447.
McCoullough et al., (2005) Ilar J., 46(3) pp. 230-240.
Mochii, M. et al. (1991) Pigment Cell Res. 4, pp. 41-47.
Old, L., Cancer Res (1981) 41, pp. 361-375.
Nijman et al. (1993), Eur. J. Immunol. 23, pp. 1215.
Padgett, R.A. et al. (1986) Ann. Rev. Biochem. 55, pp. 119-1150.
Pearson, W.R. et al. (1988) Proc. Nat'l. Acad. Sci. USA 85, pp. 2444-2448.
Proudfoot, N.J. et al. (1976) Nature 263, pp. 211-214.
Rosenberg, S.A. et al. (1986), Science 223, pp. 1318-1321.
Ruppert, J. et al. (1993) Cell 74, pp. 929.
Ruskin, B. et al. (1984) Cell 38, pp. 317-331.
Sanger, F. et al. (1977) Proc. Nat'l. Acad. Sci. USA 74, pp. 5463-5467.
Schirle et al., (2001) J. Immunol. Methods 257, pp. 1-16.
Schwartz, R.H. (1992) Cell 71, pp. 1065-1068.
Seed, B. Et al. (1987) Proc. Nat'l. Acad. Sci. USA 84, pp. 3365.
Smit, N. et al. (1993) Arch. Dermatol. Res. 285, pp. 356-365.
Topalian, S.L. et al. (1987), J. Immunol. Meth. 102, pp. 127-141.
Townsend, A.R.M. et al. (1989), Ann. Rev. Immunol. 7, pp. 601-624.
Tsomides, T.J. et al. (1991) Proc. Nat'l Acad. Sci. USA 88, pp. 11276.
Van Der Burg et al., (1996) J. immunol. 156(9), pp. 3308-3314.
Van Muijen, G.N.P. et al. (1991) Clin. Expl. Metast. 9, pp. 259-272.
Vennegoor, C. et al. (1988) Am. J. Pathol. 130, pp. 179-192.
Vogel, A.M. et al. (1988) Cancer Res. 48, pp. 1286-1294.
von Heijne, G. (1986) Nucleic Acids Res. 14, pp. 4683-4690.
Adema, G.J. et al. (1991) Biochem. Biophys. Res. Comm. 178, pp. 985-992.

MELANOMA ASSOCIATED PEPTIDE ANALOGUES AND VACCINES AGAINST MELANOMA

CROSS-REFERENCE TO RELATED APPLICATIONS

This application is a divisional of U.S. patent application Ser. No. 10/808,681, filed Mar. 25, 2004 (now abandoned), which is a continuation of application Ser. No. 09/214,836 filed Oct. 4, 1999 (now abandoned), which was the National Stage of International Application No. PCT/EP97/03712 filed Jul. 8, 1997 and having a priority date of Jul. 11, 1996. The disclosure of each of these related applications is incorporated herein their entireties.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 6,065 Byte ASCII (Text) file named "704201.5T25.TXT," created on Dec. 16, 2008.

BACKGROUND OF THE INVENTION

The present invention is concerned with cancer treatment and diagnosis, especially with melanoma associated peptide analogues, epitopes thereof, vaccines against and diagnostics for the detection of melanoma and for the monitoring of vaccination.

During the stepwise changes from normal to tumor tissue, tumor-associated antigens appear. The characteristics of tumor-associated antigens are very much dependent on the origin of the tumor carrying them. The existence of antigens associated with animal tumors was documented in the last century, and the antigenic character of human cancers has been well established, primarily through recent studies with monoclonal antibodies.

Attempts to isolate and chemically characterize these antigens have encountered serious difficulties, many having to do with a lack of reagents suitable for precipitation of the antigen-bearing molecules from a solution.

Like many other stimuli, the tumor-associated antigens activate not one but a whole set of defense mechanisms—both specific and unspecific, humoral and cellular. The dominant role in in vivo resistance to tumor growth is played by T lymphocytes. These cells recognize tumor-associated antigens presented to them by antigen presenting cells (APCs), and will be activated by this recognition, and upon activation and differentiation, attack and kill the tumor cells.

Cytotoxic T lymphocytes (CTL) recognize short peptide fragments of 9-11 amino acids in length, which are presented in the antigen-binding groove of Major Histocompatibility Complex (MHC) class I molecules (Townsend et al., 1986, *Cell* 44.959; Bjorkman et al., 1987, *Nature* 329:512). These peptides are usually derived from intracellular protein pools and associate in the lumen of the endoplasmic reticulum with MHC class I heavy chain and β2-microglobulin molecules, followed by transportation of the MHC-peptide complex to the cell surface. Despite the presence of many putative antigenic peptides within the same antigen, only a few peptides are selected for recognition by CTL.

MHC Class I/II antigens are often down regulated in solid tumors. This may affect all class I/II antigens, or only part of them. Viral and cellular peptides that can sensitize appropriate target cells for cytotoxic T lymphocyte mediated lysis may fail to do so when produced in cells with a low level of expression of MHC class I antigen. Cytotoxic sensitivity may be induced, at least in some cases by raising the level of MHC class I/II antigen expression by interferon γ and tumor necrosis factor α.

The MHC class I binding-affinity of an epitope is an important parameter determining the immunogenicity of the peptide-MHC complex. Analysis of Human histocompatibility antigen (HLA-A *0201)-restricted epitopes recognized by anti-viral CTL demonstrated that several peptides bind to HLA-A *0201 with high affinity. Furthermore, immunogenicity analysis of motif containing potential epitopes using HLA-A *0201 transgenic mice revealed that a threshold MHC class I affinity was required for a peptide in order to elicit a CTL response Messing et al., 1995, *J. Immunol.* 154: 5934; Sette et al., 1994, *J. Immunol.* 153:5586). In addition to the MHC class I-binding affinity, stability of peptide-MHC complexes at the cell surface contributes to the immunogenicity of a CTL epitope. Consequently, MHC class I binding-affinity and stability of peptide-MHC complexes are important criteria in the selection of specific peptide determinants for development of CTL-epitope based therapeutic vaccines.

Recently, a number of antigens have been identified as target antigens for anti-melanoma CTL. Using a genetic approach, the tumor specific antigens MAGE-1 and -3, as well as the melanocyte-lineage specific antigen tyrosinase, were identified (van der Bruggen et al., 1991, *Science* 254: 1643; Gaugler et al., 1994, *J. Exp. Med.* 179:921; Brichard et al., 1993, *J. Exp. Med.* 178:489).

In the co-owned and co-pending patent-application (EP 0 668 350), the gp100 melanocyte-specific protein was identified as a target antigen for melanoma tumor infiltrating lymphocytes.

Recently, two other melanocyte differentiation antigens, Melan-A/MART-1 and gp75, were identified as target antigens for anti-melanoma CTL (Coulie et al., 1994, *J. Exp. Med.* 180:35; Kawakami et al., 1994, *Proc. Natl. Acad. Sci. USA.* 91:3515; Wang et al., 1995, (vol 181, pg 799, 1995). *J. Exp. Med.* 181:1261. 10-12). Eight HLA-A *0201 restricted epitopes derived from these antigens have now been characterized, displaying varying affinities for HLA-A *0201 (Wolfel et al., 1994, *Eur. J. Immunol.* 24:759; Cox et al., 1994, *Science* 264:716; Kawakami et al. 1995. *J. Immunol.* 154.3961; Bakker et al., 1995, *Int. J. Cancer* 62:97; Kawakami et al., 1994, *J. Exp. Med.* 180:347; Castelli et al., 1995, *J. Exp. Med.* 181:363).

DISCLOSURE OF THE INVENTION

In an attempt to improve the immunogenicity of two HLA-A *0201 presented epitopes derived from the melanocyte differentiation antigens gp 100 and Melan-A/MART-1, amino acid substitutions within the epitopes to improve HLA-A *0201-binding affinity were performed.

Surprisingly, it was found that these epitope-analogues have an improved immunogenicity in view of the original epitope. Furthermore, in the present invention it is demonstrated that the epitope-analogues allow the induction of peptide-specific CTL displaying cross-reactivity with target cells endogenously processing and presenting the native epitope.

Usage of these epitope-analogues according to the present invention with improved immunogenicity may contribute to the development of CTL-epitope based vaccines in chronic viral disease and cancer.

In more detail, since MHC class I-affinity and peptide-MHC complex-stability are important parameters determining the immunogenicity of an MHC class I presented epitope, the possibility to improve the capacity of two melanocyte differentiation antigen-derived epitopes to bind to HLA-A *0201 without affecting interactions with the T-cell receptor (TCR) is explored. Detailed analysis of the Melan-A/MART-1 27-35 and gp100 154-162 epitopes using alanine substitutions revealed that amino acids at positions 4 to 7 (Melan-A/MART-1 27-35) or 5 to 7 (gp100 154-162) are critical residues for TCR recognition. These data are in line with X-ray crystallography studies of the HLA-A *0201 molecule (Saper et al., 1991, *J. Mol. Biol.* 219:277; Latron et al., 1992, *Science* 257:964), implying a role for the more permissive residues at position 4 and 5 of the peptide oriented towards the outside of the MHC molecule, as prominent TCR contact sites. It is demonstrated that for HLA-A *0201 the amino acids at positions 6 and 7 of the Melan-A/MART-1 27-35 and gp100 154-162 epitopes do not only interact with secondary pockets in the MHC peptide-binding cleft, but that they are also critical residues for TCR interaction (Ruppert et al., 1993, *Cell* 74:929; Madden et al., 1993, *Cell* 75:693).

Surprisingly, the alanine substitution at position 8 in the gp100 154-162 epitope, KTWGQYWAV (SEQ ID NO: 1), resulted in a peptide that displayed increased HLA-A *0201 affinity. Moreover, this epitope-analogue was recognized by gp100-reactive CTL at tenfold lower concentrations compared to the native epitope. These data demonstrate that amino acid substitutions at a non-anchor position can result in increased MHC class I affinity and T cell recognition.

By N-terminal anchor replacements with V, L, M or I towards the HLA-A *0201 binding-motifs were set out to identify epitope-analogues for both epitopes with improved affinity for HLA-A *0201 that were still recognized by wild type epitope-reactive CTL. For the Melan-A/MART-1 epitope, epitope-analogues were obtained with comparable (M) or improved (V, L and I) affinity for HLA-A *0201. However, all N-terminal anchor replacements resulted in decreased T cell reactivity. Apparently, in case of this epitope, the N-terminal anchoring residue affects the positioning of the side chains in the center of the peptide, thereby abrogating TCR interactions. Recently, a similar observation has been described involving an HLA-B*3501 restricted epitope of the influenza A matrix protein (Dong et al., 1-996, *Eur. J. Immunol.* 26:335). Substitution of a serine residue at position 2 of the peptide for the more common HLA-B*3501 N-terminal anchor proline, considerably enhanced binding to HLA-B*3501, but the epitope-analogue was not recognized by CTL reactive with the native epitope. Moreover, this peptide behaved as a peptide-antagonist as was demonstrated for T cell recognition of both MHC class II and class I-presented peptides (Dong et al., 1996, *Eur. J. Immunol.* 26:335; De Magistris et al., 1992, *Cell* 68:625; Klenerman et al., 1994, *Nature* 369:403). These findings illustrate that anchor residue substitutions not only affect MHC class I binding, but in some cases they may also result in a conformational change of the peptide-MHC complex, leading to an altered interaction with the TCR.

However, in case of the gp100 154-162 epitope, in addition to the alanine substituted analogue KTWGQYWAV (SEQ ID NO: 1), three anchor substituted epitope-analogues KVWGQYWQV (SEQ ID NO: 2), KLWGQYWQV (SEQ ID NO: 3), and KIWGQYWQV (SEQ ID NO: 4), with improved HLA-A*0201-affinity that were recognized by anti-gp100 CTL at tenfold lower concentrations compared to the wild type epitope were obtained. In vivo immunization experiments using HLA-A*0201/K$^b$ transgenic mice demonstrated that these epitope-analogues were immunogenic, resulting in the induction of murine CTL reactive with both the epitope-analogues and the native epitope. The immunogenicity of the epitope-analogues was expected since the peptide-MHC complex stability of both the epitope-analogues and the native epitope was comparably high.

In vitro CTL induction experiments using donor derived PBL demonstrated that epitope-analogue specific CTL could be obtained displaying cross-reactivity with tumor cells endogenously presenting the wild type epitope. In addition to T lymphocytes reactive with the wild type epitope, the T cell repertoire of healthy donors apparently also contains T cells reactive with the gp100 154-162 epitope-analogues. Analysis of TCR usage of cloned CTL reactive with the different gp100 154-162 epitope-analogues and with wild type gp100 154-162 will be informative of the spectrum of the T cell repertoire that can be used to induce CTL reactivity towards the wild type epitope. With respect to immunotherapy of cancer, activation of multiple specificities in the T cell repertoire against an antigenic tumor epitope using epitope-analogues may increase the possibility of a patient to mount a successful anti-tumor response upon immunization. In addition, modified epitopes might still elicit immune responses if tolerance against the wild-type epitope is observed.

Employment of "improved" epitopes in immunotherapy protocols increases the amount of peptide-MHC complexes at the cell surface of antigen presenting cells in vivo, and will result in enhanced priming of antigen-specific CTL. Apart from their potential ill cancer immunotherapy, usage of epitope-analogues with improved immunogenicity may contribute to the development of CTL-epitope based vaccines in chronic viral disease.

Therefore, the present invention includes peptides, immunogenic with lymphocytes directed against metastatic melanomas, characterized in that it comprises at least part of the amino-acid sequence of SEQ ID NO: 9 wherein the amino-acid at position 2 or 8 is substituted.

A preferred embodiment of the present invention are peptides, wherein at position 2 Threonine is substituted by Isoleucine, Leucine or Valine.

Another preferred embodiment of the present invention are peptides, wherein at position 8 Glutamine is substituted by Alanine.

A specific preferred embodiment of the present invention are peptides, characterized in that it comprises the amino-acid sequence of any of SEQ ID NOS: 1-4 or 32-34.

The term "peptide" refers to a molecular chain of amino acids, does not refer to a specific length of the product and if required can be modified in vivo or in vitro, for example by manosylation, glycosylation, amidation, carboxylation or phosphorylation: thus inter alia polypeptides, oligopeptides and proteins are included within the definition of peptide. In addition, peptides can be part of a (chimeric) protein or can be (part of) an RNA or DNA sequence encoding the peptide or protein.

Of course, functional derivatives as well as fragments of the peptide according to the invention are also included in the present invention. Functional derivatives are meant to include peptides which differ in one or more amino acids in the overall sequence, which have deletions, substitutions, inversions or additions. Amino acid substitutions which can be expected not to essentially alter biological and immunological activities have been described. Amino acid replacements between related amino acids or replacements which have occurred frequently in evolution are, inter alia Ser/Ala, Ser/Gly, Asp/Gly, Asp/Asn, Ile/Val (see Dayhof, M. D., Atlas of protein sequence and structure, Nat. Biomed. Res. Found., Washington D.C., 1978, vol. 5, suppl. 3). Based on this information, Lipman and Pearson developed a method for rapid and sensitive protein comparison (Science 227, 1435-1441, 1985) and determining the functional similarity between homologous polypeptides.

Furthermore, as functional derivatives of these peptides are also meant to include other peptide-analogues derived from gp100 (or Melan) that are able to induce target cell lysis by tumor infiltrating lymphocytes.

In addition, with functional derivatives of these peptides are also meant addition salts of the peptides, amides of the peptides and specifically the C-terminal amides, esters and specifically the C-terminal esters and N-acyl derivatives specifically N-terminal acyl derivatives and N-acetyl derivatives.

The peptides according to the invention can be produced synthetically, by recombinant DNA technology or by viruses, if the amino acid sequence of the peptide is encoded by a DNA sequence which is part of the virus DNA. Methods for producing synthetic peptides are well known in the art.

The organic chemical methods for peptide synthesis are considered to include the coupling of the required amino acids by means of a condensation reaction, either in homogenous phase or with the aid of a so-called solid phase. The condensation reaction can be carried out as follows:

condensation of a compound (amino acid, peptide) with a free carboxyl group and protected other reactive groups with a compound (amino acid, peptide) with a free amino group and protected other reactive groups, in the presence of a condensation agent;

condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

The most common methods for the above condensation reactions are: the carbodiimide method, the azide method, the mixed anhydride method and the method using activated esters, such as described in The Peptides, Analysis, Synthesis, Biology Vol. 1-3 (Ed. Gross, E. and Meienhofer, J.) 1979, 1980, 1981 (Academic Press, Inc.).

Production of peptides by recombinant DNA techniques is a general method which is known, but which has a lot of possibilities all leading to somewhat different results. The polypeptide to be expressed is coded for by a DNA sequence or more accurately by a nucleic acid sequence.

Also part of the invention is the nucleic acid sequence comprising the sequence encoding the peptides according to the present invention.

Preferably, the sequence encoding the peptides according to the present invention are the sequences shown in SEQ ID NOS: 1-4 and 32-34.

As is well known in the art, the degeneracy of the genetic code permits substitution of bases in a codon to result in another codon still coding for the same amino acid, e.g., the codon for the amino acid glutamic acid is both GAT and GAA. Consequently, it is clear that for the expression of a polypeptide with an amino acid sequence as shown in SEQ ID NO: 1-4, 9 or 32-34 use can be made of a derivate nucleic acid sequence with such an alternative codon composition thereby different nucleic acid sequences can be found.

"Nucleotide sequence" as used herein refers to a polymeric form of nucleotides of any length, both to ribonucleic acid (RNA) sequences and to deoxyribonucleic acid (DNA) sequences. In principle, this term refers to the primary structure of the molecule. Thus, this term includes double and single stranded DNA, as well as double and single stranded RNA, and modifications thereof.

A further part of the invention are peptides, which are immunogenic fragments of the peptide-analogues.

Immunogenic fragments are fragments which still have the ability to induce an immunogenic response, i.e., that it is either possible to evoke antibodies recognizing the fragments specifically, or that it is possible to find T lymphocytes which have been activated by the fragments. Another possibility is a DNA vaccine.

As has been said above, it has been known that the immunogenic action of tumor associated antigens is often elicited through a T cell activating mechanism (Townsend et al., 1989, H., *Ann. Rev. Immunol.* 7, 601-624). Cytotoxic T lymphocytes (CTLs) recognizing melanoma cells in a T-cell receptor (TCR)-dependent and MHC-restricted manner have been isolated from tumor-bearing patients (Knuth et al., 1992, *Cancer surveys,* 39-52). It has been shown that a peptide derived from tyrosinase, another melanocyte-specific antigen, is recognized by a CTL clone (Brichard et al., 1993, *J. Exp. Med.,* 178, 489-495).

It is known that the activation of T cells through the MHC molecule necessitates processing of the antigen of which short pieces (for example 8-12 mers) are presented to the T lymphocyte.

Preferably, the peptides according to the present invention are flanked by non-related sequences, i.e., sequences with which they are not connected in nature, because it has been found that such flanking enhances the immunogenic properties of these peptides, probably through a better processing and presentation by APCs.

Another part of the invention is formed by nucleotide sequences comprising the nucleotide sequences coding for the above mentioned peptides or an array of peptides.

Next to the use of these sequences for the production of the peptides with recombinant DNA techniques, which will be exemplified further, the sequence information disclosed in the sequence listings for the peptides according to the present invention can be used for diagnostic purposes.

From these sequences primers can be derived as basis for a diagnostic test to detect gp100 or gp100-like proteins by a nucleic acid amplification technique for instance the polymerase chain reaction (PCR) or the nucleic acid sequence based amplification (NASBA) as described in U.S. Pat. No. 4,683,202 and EP 329,822, respectively.

These nucleotide sequences can be used for the production of the peptides according to the present invention with recombinant DNA techniques. For this, the nucleotide sequence must be comprised in a cloning vehicle which can be used to transform or transfect a suitable host cell.

A wide variety of host cell and cloning vehicle combinations may be usefully employed in cloning the nucleic acid sequence. For example, useful cloning vehicles may include chromosomal, non-chromosomal and synthetic DNA sequences such as various known bacterial plasmids, and wider host range plasmids such as pBR 322, the various pUC, pGEM and pBluescript plasmids, bacteriophages, e.g. lambda-gt-Wes, Charon 28 and the M13 derived phages and vectors derived from combinations of plasmids and phage or virus DNA, such as SV40, adenovirus or polyoma virus DNA (Rodriquez et al., 1988, ed. Vectors, Butterworths; Lenstra et al., 1990, *Arch. Virol.,* 110, 1-24).

Useful hosts may include bacterial hosts, yeasts and other fungi, plant or animal hosts, such as Chinese Hamster Ovary (CHO) cells, melanoma cells, dendritic cells, monkey cells and other hosts.

Vehicles for use in expression of the peptides may further comprise control sequences operably linked to the nucleic acid sequence coding for the peptide. Such control sequences generally comprise a promoter sequence and sequences which regulate and/or enhance expression levels. Furthermore, an origin of replication and/or a dominant selection marker are often present in such vehicles. Of course, control and other sequences can vary depending on the host cell selected.

Techniques for transforming or transfecting host cells are quite known in the art (for instance, Maniatis et al., 1982/1989, *Molecular cloning: A laboratory Manual*, Cold Spring Harbor Lab.).

It is extremely practical if, next to the information for the peptide, also the host cell is co-transformed or co-transfected with a vector which carries the information for an MHC molecule to which said peptide is known to bind. Preferably, the MHC molecule is HLA-A2.1, HLA-A1 or HLA-A3.1, or any other HLA allele which is known to be present in melanoma patients. HLA-A2.1 is especially preferred because it has been established (Anichini et al., 1993, *J. Exp. Med.*, 177, 989-998) that melanoma cells carry antigens recognized by HLA-A2.1 restricted cytotoxic T cell clones from melanoma patients.

Host cells especially suited for the expression of the peptides according to the present invention are the murine EL4 and P8.15 cells. For expression of said peptides human BLM cells (Katano et al., 1984, *J. Cancer Res. Clin. Oncol.* 108, 197) are especially suited because they already are able to express the MHC molecule HLA-A2.1.

The peptides according to the present invention can be used in a vaccine for the treatment of melanoma.

In addition to an immunogenically effective amount of the active peptide, the vaccine may contain a pharmaceutically acceptable carrier or diluent.

The immunogenicity of the peptides of the invention, especially the oligopeptides, can be enhanced by cross-linking or by coupling to an immunogenic carrier molecule (i.e., a macromolecule having the property of independently eliciting an immunological response in a patient, to which the peptides of the invention can be covalently linked) or if part of a protein.

Covalent coupling to the carrier molecule can be carried out using methods well known in the art, the exact choice of which will be dictated by the nature of the carrier molecule used. When the immunogenic carrier molecule is a protein, the peptides of the invention can be coupled, e.g., using water soluble carbodiimides such as dicyclohexylcarbodiimide, or glutaraldehyde.

Coupling agents such as these can also be used to cross-link the peptides to themselves without the use of a separate carrier molecule. Such cross-linking into polypeptides or peptide aggregates can also increase immunogenicity.

Examples of pharmaceutically acceptable carriers or diluents useful in the present invention include stabilizers such as SPGA, carbohydrates (e.g., mannose, sorbitol, mannitol, starch, sucrose, glucose, dextran), proteins such as albumin or casein, protein containing agents such as bovine serum or skimmed milk and buffers (e.g., phosphate buffer).

Optionally, one or more compounds having adjuvant activity may be added to the vaccine. Suitable adjuvants are for example aluminium hydroxide, phosphate or oxide, oil-emulsions (e.g. of Bayol F® or Marcol 52®), saponins or vitamin-E solubilisate.

Dendritic cells are professional APC that express mannose receptor used to take up antigen thus facilitating antigen processing.

The vaccine according to the present invention can be given inter alia intravenously, intraperitoneally, intranasally, intradermally, subcutaneously or intramuscularly.

The useful effective amount to be administered will vary depending on the age and weight of the patient and mode of administration of the vaccine.

The vaccine can be employed to specifically obtain a T cell response, but it is also possible that a B cell response is elicited after vaccination. If so, the B cell response leads to the formation of antibodies against the peptide of the vaccine, which antibodies will be directed to the source of the antigen production, i.e., the tumor cells. This is an advantageous feature, because in this way the tumor cells are combated by responses of both the immunological systems.

Both immunological systems will even be more effectively triggered when the vaccine comprises the peptides as presented in an MHC molecule by an antigen presenting cell (APC). Antigen presentation can be achieved by using monocytes, macrophages, interdigitating cells, Langerhans cells and especially dendritic cells, loaded with one of the peptides of the invention or loading with protein including peptide or manosylated protein. Loading of the APCs can be accomplished by bringing the peptides of the invention into or in the neighborhood of the APC, but it is more preferable to let the APC process the complete gp100 antigen. In this way a presentation is achieved which mimics the in vivo situation most realistically. Furthermore, the MHC used by the cell is of the type which is suited to present the epitope.

An overall advantage of using APCs for the presentation of the epitopes is the choice of APC cell that is used in this respect. It is known from different types of APCs that there are stimulating APCs and inhibiting APCs.

Preferred APCs include, but are not limited to, the listed cell types, which are so-called "professional" antigen presenting cells, characterized in that they have co-stimulating molecules, which have an important function in the process of antigen presentation. Such co-stimulating molecules are, for example, B7, CD25, CD40, CD70, CTLA-4 or heat stable antigen (Schwartz, 1992, *Cell* 71, 1065-1068).

Fibroblasts, which have also been shown to be able to act as an antigen presenting cell, lack these co-stimulating molecules.

It is also possible to use cells already transfected with a cloning vehicle harboring the information for the melanocyte peptide analogues and which are cotransfected with a cloning vehicle which comprises the nucleotide sequence for an MHC class I molecule, for instance the sequence coding for HLA A2.1, HLA A1 or HLA A3.1. These cells will act as an antigen presenting cell and will present peptide analogues in the MHC class I molecules which are expressed on their surface. It is envisaged that this presentation will be enhanced, when the cell is also capable of expressing one of the above-mentioned co-stimulating molecules (in particular B7 (B7.1, B7.2), CD40), or a molecule with a similar function (e.g., cytokines transfected in cell line). This expression can be the result of transformation or transfection of the cell with a third cloning vehicle having the sequence information coding for such a co-stimulating molecule, but it can also be that the cell already was capable of production of co-stimulating molecules.

Instead of a vaccine with these cells, which next to the desired expression products, also harbor many elements which are also expressed and which can negatively affect the desired immunogenic reaction of the cell, it is also possible that a vaccine is composed with liposomes which expose MHC molecules loaded with peptides, and which, for instance, are filled with lymphokines. Such liposomes will trigger an immunologic T cell reaction.

By presenting the peptide in the same way as it is also presented in vivo, an enhanced T cell response will be evoked. Furthermore, by the natural adjuvant working of the relatively large, antigen presenting cells also a B cell response is triggered. This B cell response will also lead to the formation of antibodies directed to the peptide-MHC complex. This complex is especially found in tumor cells, where it has been shown that in the patient epitopes of gp100 are presented naturally, which are thus able to elicit a T cell response. It is this naturally occurring phenomenon which is enlarged by the vaccination of APCs already presenting the peptides of the invention. By enlarging not only an enlarged T cell response will be evoked, but also a B cell response which leads to antibodies directed to the MHC-peptide complex will be initiated.

The vaccines according to the invention can be enriched by numerous compounds which have an enhancing effect on the initiation and the maintenance of both the T cell and the B cell response after vaccination.

In this way, addition of cytokines to the vaccine will enhance the T cell response. Suitable cytokines are for instance interleukins, such as IL-2, IL-4, IL-7, or IL-12, GM-CSF, RANTES, MIP-α, and tumor necrosis factor, and interferons, such as IFN- or the chemokins.

In a similar way, antibodies against T cell surface antigens, such as CD2, CD3, CD27 and CD28 will enhance the immunogenic reaction.

Also, the addition of helper epitopes to stimulate CD4$^+$ helper cells or CD8$^+$ killer cells augments the immunogenic reaction. Alternatively, also helper epitopes from other antigens can be used, for instance from heat shock derived proteins or cholera toxin.

Another part of the invention is formed by using reactive tumor infiltrating lymphocytes (TILs) directed against the peptides according to the present invention. In this method, the first step is taking a sample from a patient. This is usually done by resection of a tumor deposit under local anesthesia. The TILs present in this specimen are then expanded in culture for four to eight weeks, according to known methods (Topalian et al., 1987, *J. Immunol. Meth.* 102, 127-141). During this culture, the TILs are then checked for reactivity with the peptides according to the present invention or gp100-protein. The TILs which recognize the antigen are isolated and cultured further.

The reactive tumor infiltrating lymphocytes which are obtained through this method, also form part of the invention. An example of such TIL cell line, designated TIL 1200, has been found which specifically reacts with gp100 and its epitopes. This TIL 1200 cell line also expresses the MHC molecule HLA-A2.1. Furthermore, expression of TCR α/β, CD3 and CD8 by this cell line has been demonstrated. Furthermore, TIL 1200 recognizes transfectants expressing both HLA-A2.1 and gp100.

TIL 1200 and other TILs recognizing gp100 are suited for treatment of melanoma patients. For such treatment, TILs may be cultured as stated above, and they are given back to the patients by an intravenous infusion. The success of treatment can be enhanced by pre-treatment of the tumor bearing host with either total body radiation or treatment with cyclophosphamide and by the simultaneous administration of interleukin-2 (Rosenberg et al., 1986, *Science* 223, 1318-1321).

The TILs infused back to the patient are preferably autologous TILs (i.e., derived from the patient's own tumor) but also infusion with allogenic TILs can be imagined.

A further use of the TILs obtained by the method as described above is for in vivo diagnosis. Labeling of the TILs, for instance with $^{111}$In (Fisher et al., 1989, *J. Clin. Oncol.* 7, 250-261) or any other suitable diagnostic marker, renders them suited for identification of tumor deposits in melanoma patients.

Another part of the invention is formed by the T cell receptor (TCR) expressed by reactive CTLs directed against the peptides according to this invention or the gp100-protein. As is well known in the art, the TCR determines the specificity of a CTL. Therefore, the cDNA encoding the TCR, especially its variable region, can be isolated and introduced into T cells, thereby transferring anti-tumor activity to any T cell. Especially introduction of such a TCR into autologous T cells and subsequent expansion of these T cells will result in large numbers of CTL suitable for adoptive transfer into the autologous patient.

Cells harboring this T cell receptor can also be used for vaccination purposes.

A vaccine can also be composed from melanoma cells capable of expression of the peptides according to the present invention. It is possible to isolate these cells from a patient, using specific antibodies, such as NKI-beteb (directed against gp100), but is also possible to produce such melanoma cells from cultured melanoma cell lines, which either are natural gp100-producers or have been manipulated genetically to produce the peptides according to the present invention. These cells can be irradiated to be non-tumorogenic and infused (back) into the patient. To enhance the immunologic effect of these melanoma cells it is preferred to alter them genetically to produce a lymphokine, preferably interleukine-2 (IL-2) or granulocyte-macrophage colony stimulation factor (GM-CSF). Peptide$^+$/gp100$^+$ melanoma cells can be transfected with a cloning vehicle having the sequence coding for the production of IL-2 or GM-CSF.

Infusion of such a vaccine into a patient will stimulate the formation of CTLs.

Another type of vaccination having a similar effect is vaccination with pure DNA, for instance the DNA of a vector or a vector virus having the DNA sequence encoding the peptides according the present invention (both homologues and heterologues (chimeric protein) or repetitive). Once injected, the virus will infect or the DNA will be transformed to cells which express the antigen or the peptide(s).

Antibodies directed against the peptides according to the present invention are also part of the invention.

Monospecific antibodies to these peptides can be obtained by affinity purification from polyspecific antisera by a modification of the method of Hall et al. (1984, *Nature* 311, 379-387). Polyspecific antisera can be obtained by immunizing rabbits according to standard immunization schemes.

Monospecific antibody as used herein is defined as a single antibody species or multiple antibody species with homogeneous binding characteristics for the relevant antigen. Homogeneous binding as used herein refers to the ability of the antibody species to bind to ligand binding domain of the invention.

The antibody is preferably a monoclonal antibody, more preferably a humanized monoclonal antibody.

Monoclonal antibodies can be prepared by immunizing inbred nice, preferably Balb/c with the appropriate protein by techniques known in the art (Köhler, G. and Milstein C., 1975, *Nature* 256, 495-497). Hybridoma cells are subsequently selected by growth in hypoxanthine, thymidine and aminopterin in an appropriate cell culture medium such as Dulbecco's modified Eagle's medium (DMEM). Antibody producing hybridomas are cloned, preferably using the soft agar technique of MacPherson (1973, *Tissue Culture Methods and Applications*, Kruse and Paterson, eds., Academic Press). Discrete colonies are transferred into individual wells of culture plates for cultivation in an appropriate culture medium. Antibody producing cells are identified by screening with the appropriate immunogen. Immunogen positive hybridoma cells are maintained by techniques known in the art. Specific anti-monoclonal antibodies are produced by cultivating the hybridomas in vitro or preparing ascites fluid in mice following hybridoma injection by procedures known in the art.

It may be preferred to use humanized antibodies. Methods for humanizing antibodies, such as CDR-grafting, are known (Jones et al., 1986, *Nature* 321, 522-525). Another possibility to avoid antigenic response to antibodies reactive with polypeptides according to the invention is the use of human antibodies or fragments or derivatives thereof.

Human antibodies can be produced by in vitro stimulation of isolated B-lymphocytes, or they can be isolated from (immortalized) B-lymphocytes which have been harvested from a human being immunized with at least one ligand binding domain according to the invention.

Antibodies as described above can be used for the passive vaccination of melanoma patients. A preferred type of antibodies for this kind of vaccine are antibodies directed against the above-mentioned peptides presented in connection with the MHC molecule. To produce these kind of antibodies immunization of peptides presented by APCs is required. Such an immunization can be performed as described above. Alternatively, human antibodies to peptide-MHC complexes can be isolated from patients treated with a vaccine consisting of APCs loaded with one of said peptides.

The antibodies, which are formed after treatment with one of the vaccines of the invention can also be used for the monitoring of said vaccination. For such a method, serum of the patients is obtained and the antibodies directed to the peptide with which has been vaccinated are detected. Knowing the antibody titre from this detection, it can be judged if there is need for a boost vaccination.

Specific detection of said antibodies in the serum can be achieved by labeled peptides. The label can be any diagnostic marker known in the field of in vitro diagnosis, but most preferred (and widely used) are enzymes, dyes, metals and radionuclides, such as $^{67}$Ga, $^{99m}$TC, $^{111}$In, $^{113m}$In, $^{123}$I, $^{125}$I, or $^{131}$I.

The radiodiagnostic markers can be coupled directly to the peptides of the invention or through chelating moieties which have been coupled to the peptide directly or through linker or spacer molecules. The technique of coupling of radionuclides to peptides or peptide-like structures is already known in the field of (tumor) diagnostics from the numerous applications of labeled antibodies used both in in vivo and in in vitro tests.

Direct labeling of peptides can, for instance, be performed as described in the one-vial method (Haisma et al., 1986, *J. Nucl. Med.* 27, 1890). A general method for labeling of peptides through chelators, with or without linker or spacer molecules, has, for instance, been described in U.S. Pat. Nos. 4,472,509 and 4,485,086. Chelators using a bicyclic anhydride of DTPA have been disclosed in Hnatowich et al. (1983, *J. Immunol. Meth.* 65, 147-157). Coupling through diamide dimercaptide compounds has been disclosed in EP 188,256.

BRIEF DESCRIPTION OF THE SEVERAL VIEWS OF THE DRAWINGS

The present invention is further described by way of examples with reference to the accompanying figures, in which.

DETAILED DESCRIPTION OF THE INVENTION

Materials and Methods

Figure 1:
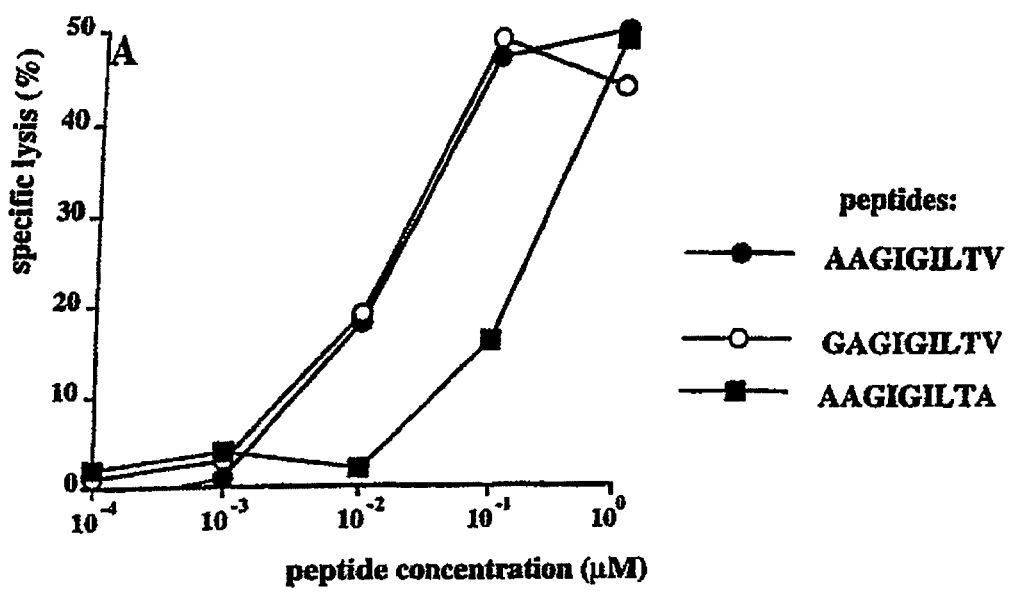
FIG. 1. Target cell sensitization of alanine replacement epitopes. (A) Chromium labeled T2 target cells were preincubated for 1 hour with various amounts of the indicated alanine-substituted epitope-analogues AAGIGILTV (SEQ ID NO: 8); GAGIGILTV (SEQ ID NO: 10); and AAGIGILTA (SEQ ID NO: 25). Melan-A/MART-1 27-35-reactive TIL 1235 lymphocytes were added at an effector to target ratio of 20. (B) Target cell sensitization of alanine-substituted gp100 154-162-analogues KTWGQYWQV (SEQ ID NO: 9); ATWGQYWQV (SEQ ID NO: 11); KAWGQYWQV (SEQ ID NO: 13) KTAGQYWQV (SEQ ID NO: 15); KTWAQYWQV (SEQ ID NO: 17); KTWGQYWAV (SEQ ID NO: 1); and KTWGQYWQA (SEQ ID NO: 26) was analyzed using gp100-reactive TIL 1200 lymphocytes at an effector to target ratio of 20.
Figure 1:
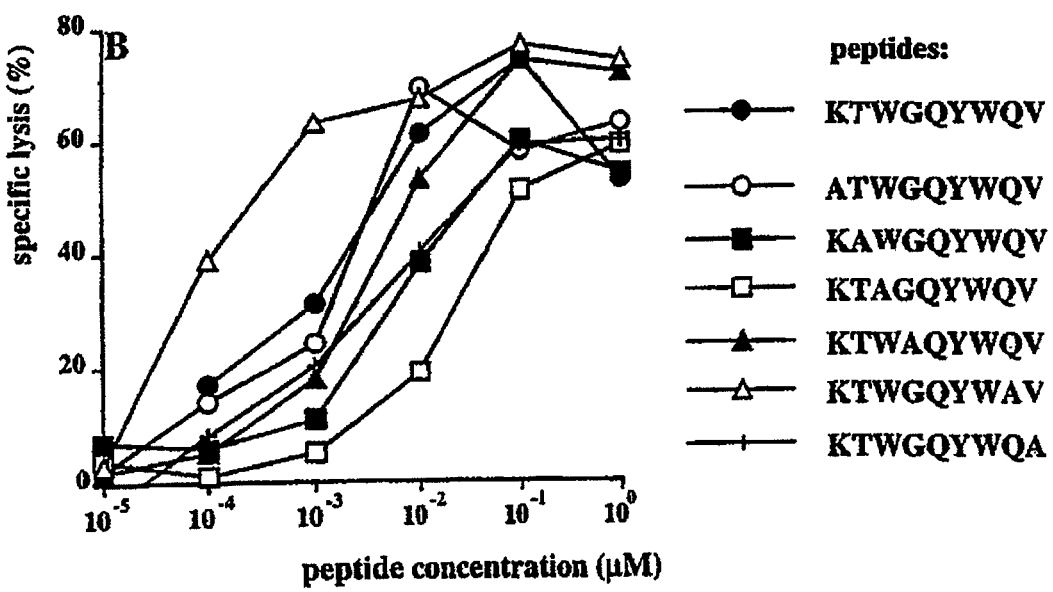

Cell Culture.

The HLA-A*0201+ melanoma line BLM was cultured as described previously (Bakker et al., 1994, *J. Exp. Med.* 179: 1005). TIL 1200 and TIL 1235 lymphocytes were cultured as was reported previously (Kawakami et al., 1992, *J. Immunol.* 148:638). T2 cells (Salter et al., 1985, *Immunogenetics.* 21:235) and HLA-A*0201+ B lymphoblastoid JY cells were maintained in Iscoves medium (Gibco, Paisley, Scotland UK) supplemented with 5% FCS (BioWhittaker, Verviers, Belgium). Jurkat A*0201/$K^b$ cells (Irwin et al., 1989, *J. Exp. Med.* 170:1091) expressing the HLA-A*0201/$K^b$ chimeric molecule were cultured in Iscoves medium with 5% FCS supplemented with 0.8 mg/ml G418 (Gibco, Paisley, Scotland UK).

HLA-A*0201+ Lymphocytes.

Healthy caucasian volunteers were phenotyped HLA-A by flow cytometry using mAbs BB7.2 (Parham et al., 1981, *Hum. Immunol.* 3:277) and MA2.1 (Parham et al., 1978, *Nature* 276:397). The donors underwent leukapheresis and PBMC were isolated by Ficoll/Hypaque density gradient centrifugation. The cells were cryopreserved in aliquots of $4\times10^7$ PBMC.

Transgenic Mice

HLA-A*0201/$K^b$ transgenic mice were used (animal distributor Harlan Sprague Dawley, Inc., Indianapolis, USA). Mice were held under clean conventional conditions. The transgenic mice express the product of the HLA-A*0201/$K^b$ chimeric gene in which the α3 domain of the heavy chain is replaced by the corresponding murine H-2 $K^b$ domain while leaving the HLA-A*0201 α1 and α2 domains unaffected (Vitiello et al., 1991, *J. Exp. Med.* 1007). This allows the murine CD8 molecule on the murine CD8+ T lymphocytes to interact with the syngeneic α3 domain of the hybrid MHC class I molecule.

Peptides.

For induction of CTL and chromium-release assays, peptides were synthesized with a free carboxy-terminus by Fmoc peptide chemistry using an ABIMED multiple synthesizer. All peptides were >90% pure as indicated by analytical HPLC. Peptides were dissolved in DMSO and stored at −20° C.

HLA-A*0201 Upregulation on T2 Cells.

Peptide-induced HLA-A*0201 upregulation on T2 cells was performed as described previously (Nijman et al., 1993, *Eur. J. Immunol.* 23:1215). Briefly, peptides were diluted from DMSO stocks to various concentrations (final DMSO concentration 0.5%) and were incubated together with $10^5$ T2 cells for 14 hours at 37° C., 5% $CO_2$ in serum-free Iscoves medium in a volume of 100 ml in the presence of 3 mg/ml human β2-microglobulin (Sigma, St Louis, Mo.). Stabilization of HLA-A*0201 molecules at the cell surface of T2 cells was analyzed by flow cytometry using anti-HLA-A2 mAb BB7.2 (Parham et al., 1981, *Hum. Immunol.* 3:277). The Fluorescence Index is expressed as: (experimental mean fluorescence÷background mean fluorescence)−1. The background mean fluorescence values were obtained by incubating T2 cells with a HLA-A*0201 non-binding peptide at similar concentrations.

Competition Based HLA-A*0201 Peptide-Binding Assay.

Peptide-binding to HLA-A*0201 was analyzed using HLA-A*0201+ JY cells as was described previously (van der Burg et al., 1995, *Hum. Immunol.* 44:189). Briefly, mild-acid treated JY cells were incubated with 150 nM Fluorescein (FL)-labeled reference peptide (FLPSDC(-FL)FPSV) and with several concentrations of competitor peptide for 24 hours at 4° in the presence of 1.0 mg/ml β2-microglobulin (Sigma, St. Louis, Mo.). Subsequently, the cells were washed, fixed with paraformaldehyde and analyzed by flow cytometry. The mean-fluorescence (MF) obtained in the absence of competitor peptide was regarded as maximal binding and equated to 0%; the MF obtained without reference peptide was equated to 100% inhibition. % inhibition of binding was calculated using the formula: (1−(MF 150 nM reference & competitor peptide−MF no reference peptide)÷(MF 150 nM reference peptide−MF no reference peptide))×100%. The binding capacity of competitor peptides is expressed as the concentration needed to inhibit 50% of binding of the FL-labeled reference peptide ($IC_{50}$).

Measurement of MHC-Peptide Complex Stability at 37° C.

Measurement of MHC-peptide complex stability was performed. HLA-A*0201+ homozygous JY cells were treated with $10^{-4}$ M emetine (Sigma, St. Louis, USA) for 1 hour at 37° C. to stop de novo synthesis of MHC class I molecules. The cells were then mild-acid treated and subsequently loaded with 200 mM of peptide for 1 hour at room temperature. Thereafter, the cells were washed twice to remove free peptide and were incubated at 37° C. for 0, 2, 4 and 6 hours. Subsequently, the cells were stained using mAb BB7.2 (Parham et al., 1981, *Hum. Immunol.* 3:277), fixed with paraformaldehyde and analyzed by flow cytometry.

CTL Induction in HLA-A*0201/$K^b$ Transgenic Mice.

Groups of 3 HLA-A*0201/$K^b$ transgenic mice were injected subcutaneously in the base of the tail vein with 100 mg peptide emulsified in IFA in the presence of 140 mg of the H-2 I-$A^b$-restricted HBV core antigen-derived T helper epitope (128-140; sequence TPPAYRPPNAPIL) (Milich et al., 1988, *Proc. Natl. Acad. Sci. U.S.A.* 85:1610). After 11 days, mice were sacrificed and spleen cells ($30\times10^6$ cells in 10 ml) were restimulated in vitro with peptide-loaded syngeneic irradiated LPS-stimulated B cell lymphoblasts (ratio 4:1). At day 6 of culture, the bulk responder populations were tested for specific lytic activity.

HLA-A*0201+ Donor Derived CTL Induction In Vitro

Using thawed PBMC, dendritic cells were generated according to the procedure of Romani et al. (Romani et al., 1994, *J. Exp. Med.* 180:83) as was described previously (Bakker et al., 1995, *Cancer Res.* 55:5330). Before the onset of culture, dendritic cells were loaded with 50 mM of peptide. Autologous CD8+ enriched responder T lymphocytes were prepared by adhering thawed PBMC for 2 hours and by subsequent partial depletion of the non-adherent fraction of CD4+ T cells using the anti-CD4 mAb RIV-7 (Leerling et al., 1990, *Dev. Biol. Stand.* 71:191) and Sheep-anti-Mouse-IgG coated magnetic beads (Dynal, Oslo, Sweden). At the onset of stimulation, $2\times10^5$ peptide-loaded DC and $2\times10^6$ responder cells were co-cultured per well of a 24-well tissue culture plate (Costar, Badhoevedorp, The Netherlands) in 2 ml of Iscoves medium containing 5% pooled human AB+ serum, $10^3$ U/ml IL-6 (Sandoz, Basel, Switzerland) and 5 ng/ml IL-12.

On day 8 and day 15, the responder populations were restimulated using peptide-pulsed dendritic cells as stimulator cells. The cultures were propagated in medium containing IL-2 (Cetus Corp., Emeryville, Calif.) and IL-7 (Genzyme, Cambridge, Mass.) at final concentrations of 10 U/ml and 5 ng/ml respectively. Weekly hereafter the cultures were restimulated using adherent peptide-pulsed PBMC as was described previously (Bakker et al., 1995, *Cancer Res.* 55:5330). Responder populations were tested for specific lytic activity after at least 4 rounds of restimulation.

Chromium-Release Assay.

Chromium release assays were performed as described previously (Bakker et al., 1994, *J. Exp. Med.* 179:1005.). Briefly, $10^6$ target cells were incubated with 100 mCi $Na_2^{51}CrO_4$ (Amersham, Bucks, UK) for 1 hour. Various amounts of effector cells were then added to the target cells in triplicate wells of U bottomed microtiter plates (Costar, Badhoevedorp, The Netherlands) in a final volume of 150 ml. In peptide recognition assays, target cells were pre-incubated with various concentrations of peptide for 30 or 60 min at 37° C. in a volume of 100 ml prior to the addition of effector cells. After 5 h of incubation, part of the supernatant was harvested and its radioactive content was measured. The mean percentage specific lysis of triplicate wells was calculated using the formula: % specific lysis=((experimental release−spontaneous release)÷(maximal release−spontaneous release))×100.

Example 1

Identification of Amino Acid Residues Engaged in HLA-A*0201 Binding and/or TCR Interactions for the Melan-A/MART-1 27-35 and the gp100 154-162 Epitopes The Melan-A/MART-27-35 and the gp100 154-162 epitopes have been identified using HLA-A*0201 restricted TIL lines derived from metastatic melanomas. The Melan-A/MART-1 27-35 epitope was found to be the nominal epitope capable of triggering the Melan-A/MART-1 specific TIL 1235 line when presented on HLA-A*0201+ target cells (Kawakami et al., 1994. *J. Exp. Med.* 180:347). Among a panel of peptides ranging from 8-mers to 11-mers located around gp100 amino acids 155-161, we identified the 9-mer 154-162 as the peptide most efficient in sensitizing HLA-A*0201+ target cells for lysis by the gp100 reactive TIL 1200 line (Balder et al., 1995, *Int. J. Cancer* 62:97). Both the Melan-A/MART-1 27-35 9-mer and the gp100 154-162 9-mer have now been eluted from the cell surface of HLA-A*0201+ melanoma cells, and were identified by tandem mass-spectroscopy, indicating that they are indeed the nominal epitopes endogenously presented in HLA-A*0201. To identify amino acid residues in both epitopes engaged in HLA-A*0201 binding and/or TCR interactions, epitope-analogues were synthesized in which the native amino acid was replaced by an alanine residue. In case alanine residues were present in the wild type epitope, they were substituted for the amino acid glycine. The substituted peptides were assayed for binding to HLA-A*0201 by means of an indirect binding assay using the processing defective cell line T2 (Nijman et al., 1993, *Eur. J. Immunol.* 23:1215). All substitutions in the Melan-A/MART-1 epitope resulted in a nearly complete loss in the capability to stabilize HLA-A*0201 molecules at the cell surface of T2 cells (Table I). When the Melan-A/MART-1 27-35 analogues were used at micromolar concentrations to sensitize HLA-A*0201+ target cells for lysis by Melan-A/MART-1-specific CTL, we observed a decrease in target cell lysis for the alanine replacements at positions 4 to 7 of the epitope (Table I). In addition, the glycine substitution at position 2 resulted in decreased CTL reactivity. The amino acids at these positions in the Melan-A/MART-1 27-35 epitope are therefore most likely involved in TCR interactions.

In case of the gp100 154-162 epitope decreased HLA-A*0201 affinity of epitope-analogues was only observed for the alanine substitutions at position 3 and 9 (Table 1). With respect to T cell recognition, alanine substitutions at positions 5, 6 and 7 of the epitope were not allowed, indicating that amino acids at these positions are critical contact residues within this epitope for the TCR.

Subsequently, the epitope-analogues that induced reactivity at micromolar concentrations were titrated to evaluate their relative ability to sensitize T2 target cells for lysis by the relevant CTL (FIG. 1). In all cases the epitope-analogues were similar or inferior compared to the wild type epitope in their sensitizing capacity, except for the alanine substitution at position 8 of the gp100 154-162 epitope. Surprisingly, this peptide was able to induce target cell lysis by gp100-reactive CTL even at a tenfold lower concentration.

Example 2

N-Terminal Anchor Residue Replacements in Both the gp100 154-162 and the Melan-A/MART-1 27-35 Epitopes Result in Improved Affinity for HLA-A*0201

Figure 2:
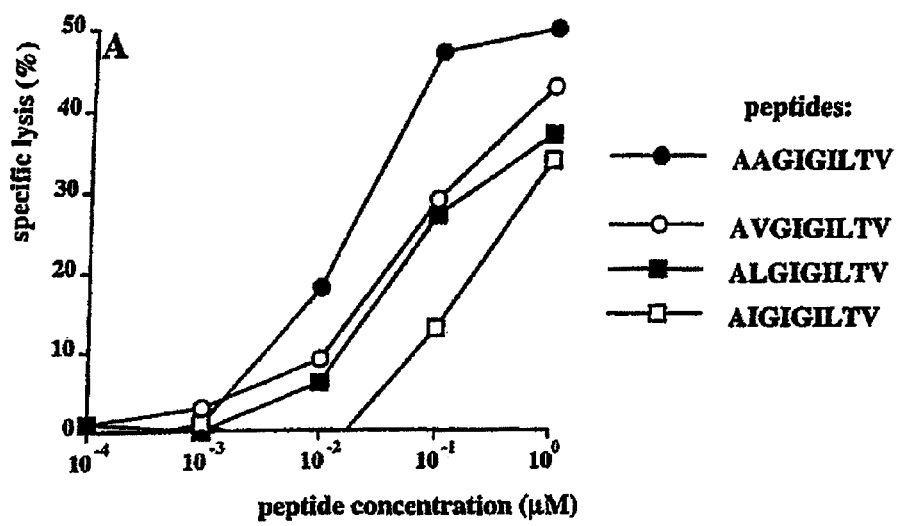
FIG. 2. Target cell sensitization of N-terminal anchor-replacement epitopes. Chromium release experiments were performed as in FIG. 1. (A) Melan-A/MART-1 27-35-reactive TIL 1235 lymphocytes were used to assay target cell sensitization by the Melan-A/MART-1 27-35 analogues AAGIGILTV (SEQ ID NO: 8); AVGIGILTV (SEQ ID NO: 27); ALGIGILTV (SEQ ID NO: 28); and AIGIGILTV (SEQ ID NO: 30). (B) Gp100 154-162-reactive TIL 1200 lymphocytes were used to assay target cell sensitization by the gp100 154-162-analogues KTWGQYWQV (SEQ ID NO: 9); KVWGQYWQV (SEQ ID NO: 2); KLWGQYWQV (SEQ ID NO: 3); KMWGQYWQV (SEQ ID NO: 35); and KIWGQYWQV (SEQ ID NO: 4).
Figure 2:
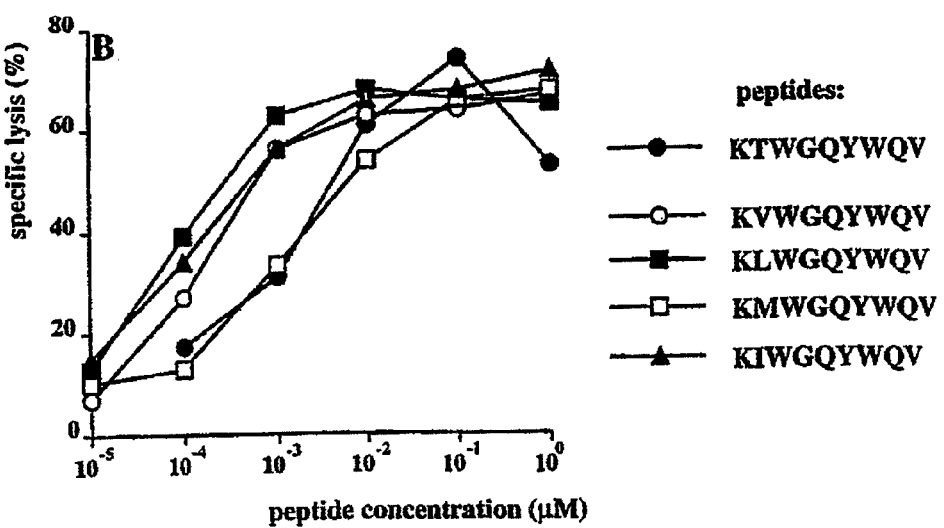

Since both the Melan-A/MART-1 27-35 and the gp100 154-162 epitopes have non-conventional N-terminal anchoring residues, we replaced these residues for the common HLA-A*0201 anchoring residues V, L, I or M (Drijfhout et al., 1995, *Hum. Immunol.* 43:1). Subsequently, we tested these peptides for HLA-A*0201 binding and their ability to sensitize target cells for lysis by the relevant CTL. Apart from the methionine substitution, all anchor residue replacements in the Melan-A/MART-1 epitope resulted in significantly improved binding to HLA-A*0201 (Table II). HLA-A*0201+ target cells loaded with these peptides at a concentration of 1 mM were recognized by the Melan-A/MART-1 reactive CTL, except for the methionine substituted epitope (Table II). Although this peptide did bind to HLA-A*0201 at a level comparable to the wild type epitope, it failed to induce CTL reactivity. Titration experiments using the Melan-A/MART-1 anchor replacement peptides demonstrated that these epitope-analogues were inferior to wild type in sensitizing target cells for lysis by TIL 1235 (FIG. 2).

Using the T2 assay all gp100 154-162 anchor replacement peptides except the methionine substituted epitope showed HLA-A*0201 binding comparable to the wild type epitope (Table II). Interestingly, these peptides were recognized by TIL 1200 when loaded on target cells at tenfold lower concentrations compared to the wild type peptide (FIG. 2), while the methionine substituted peptide showed no difference. These findings demonstrate that amino acid substitutions within the native epitope can result in improved T cell recognition.

Example 3

Improved Target Cell Sensitization by gp100 154-162 Epitope Analogues Correlates with Increased Affinity for HLA-A*0201

To assess whether the augmented CTL recognition of the substituted gp100 154-162 epitopes could be attributed to improved HLA-A*0201 affinity, the HLA-A*0201 binding capacity of these peptides was tested now using a more sensitive cell-bound HLA-A*0201 binding assay based on competition of a labeled reference peptide with the peptides of interest (van der Burg et al., 1995, *Hum. Immunol.* 44:189). HLA-A*0201 binding-affinities obtained with this assay demonstrated that all peptides that were able to sensitize target cells for lysis by TIL 1200 at tenfold lower concentrations compared to wild type, also bound with higher affinity to HLA-A*0201 (Table III). In addition to the N-terminal anchor substitutions, replacement of a polar residue for a hydrophobic residue adjacent to the C-terminal anchoring position also resulted in an epitope-analogue with improved HLA-A*0201 affinity (KTWGQYWAV (SEQ ID NO: 1)), apparently without affecting TCR recognition. Measurement of MHC class I-peptide complex dissociation rates demonstrated that the epitope-analogues tested are at least equally stable when compared to wild type (Table III). All peptides tested showed a $DT_{50}$ (the time required for 50% of the complexes to decay) longer than 4 hours. Peptides with $DT_{50}$ values of ≧3 hours were immunogenic in HLA-A*0201/$K^b$ transgenic mice. Taken together, these data indicate that the gp100 154-162 epitope-analogues may have similar or increased immunogenicity compared to wild type gp100 154-162.

Example 4

Figure 3:
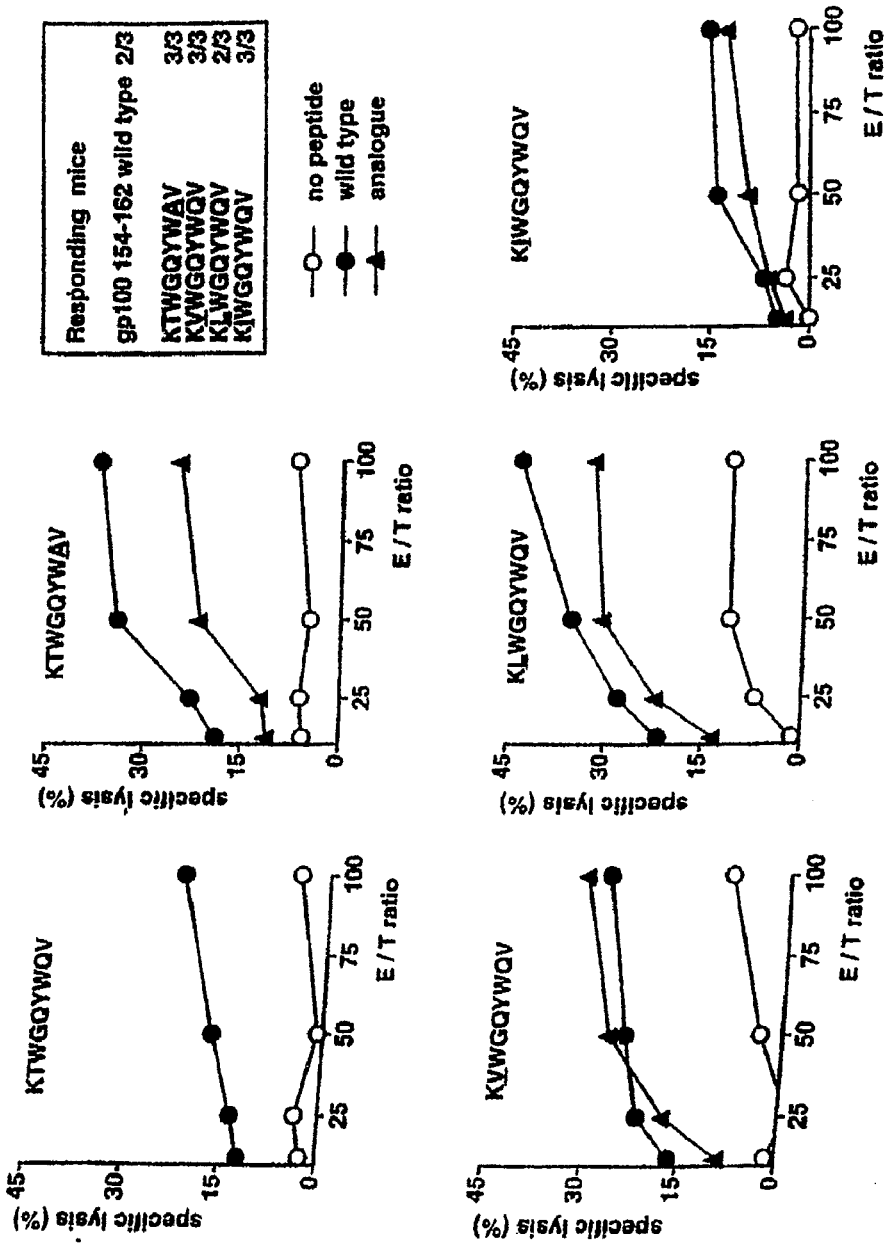
FIG. 3. Immunogenicity of gp100 154-162 epitope-analogues in HLA-A*0201/K$^b$ transgenic mice. Bulk CTL obtained from immunized mice were tested for lytic activity using chromium labeled Jurkat A2/K$^b$ target cells that were preincubated with no peptide, 10 mM wild type gp100 154-162 KTWGQYWQV (SEQ ID NO: 9) or 10 mM of the epitope-analogue KTWGQYWAV (SEQ ID NO: 1); KVWGQYWQV (SEQ ID NO: 2); KLWGQYWQV (SEQ ID NO: 3); and KIWGQYWQV (SEQ ID NO: 4) used to immunize the mice. For each peptide the mean specific lysis of bulk CTL of the responding mice is shown. Standard deviations never exceeded 15% of the mean value. One representative experiment out of two is shown.

Immunogenicity of gp100 154-162 Epitope-Analogues in HLA-A*0201/$K^b$ Transgenic Mice In order to determine the in vivo immunogenicity of the gp100 154-162 epitope-analogues of which the MHC class I binding-affinity and dissociation rate was measured. HLA-A*0201/$K^b$ transgenic mice were vaccinated with the gp100 154-162 wild type epitope, with the epitope-analogues KTWGQYWAV (SEQ ID NO: 1), KVWGQYWQV (SEQ ID NO: 2), KLWGQYWQV (SEQ ID NO: 3) or KIWGQYWQV (SEQ ID NO: 4), or with a control peptide (HBV core 18-27: FLPSDDFPSV (SEQ ID NO: 6)). The generation of these transgenic mice (Vitiello et al., 1991. *J. Exp. Med.* 173:1007) and their use to analyze in vivo immunogenicity have been described previously (Ressing et al., 1995, *J. Immunol.* 154:5934; Sette et al., 1994, *J. Immunol.* 153:5586). As shown in FIG. 3, the gp100 154-162 epitope-analogues KTWGQYWAV (SEQ ID NO: 1), KVWGQYWQV (SEQ ID NO: 2), and KLWGQYWQV (SEQ ID NO: 3), very efficiently induced a CTL response. To a lesser extent also the epitope-analogue KIWGQYWQV (SEQ ID NO: 4) and the wild type gp100 154-162 were able to elicit a CTL response. Bulk CTL derived from mice vaccinated with the gp100 154-162 epitope-analogues specifically lysed Jurkat A*0201/$K^b$ cells loaded with both the peptide used for vaccination and the wild type epitope. Interestingly, CTL bulk cultures raised against the epitope-analogues all recognized target cells pulsed with the wild type epitope equally well or better compared to target cells pulsed with epitope-analogues used for vaccination. Thus, all gp100 154-162 epitope-analogues tested were immunogenic in HLA-A*0201/b transgenic mice, and elicited CTL displaying cross-reactivity with the native gp100 154-162 epitope.

Example 5

In Vitro Induction of gp100 154-162 Epitope-Analogue Specific Human CTL Displaying Cross-Reactivity with Endogenously HLA-A*0201 Presented Wild Type gp100 154-162

Figure 4:
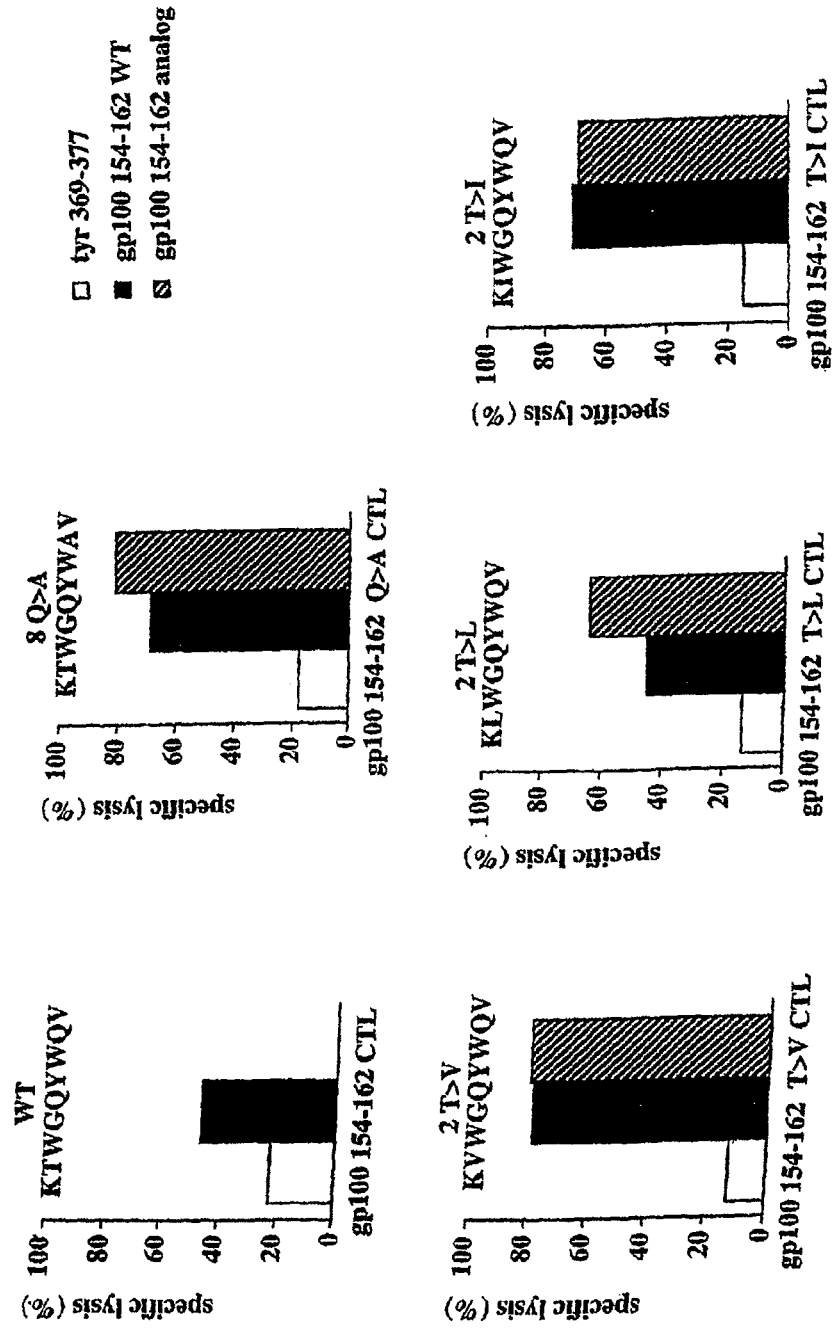
FIG. 4. Peptide specific reactivity of in vitro induced epitope-analogue specific CTL cultures. Chromium-labeled HLA-A*0201$^+$ T2 target cells were pre-incubated with 10 mM of an irrelevant HLA-A*0201-binding peptide, 10 mM wild type gp100 154-162 KTWGQYWQV (SEQ ID NO: 9) or 10 mM of the epitope-analogue KTWGQYWAV (SEQ ID NO: 1); KVWGQYWQV (SEQ ID NO: 2); KLWGQYWQV (SEQ ID NO: 3); and KIWGQYWQV (SEQ ID NO: 4) used for CTL induction. The different CTL cultures were added at an effector to target ratio of 20:1. One representative experiment out of two is shown.
Figure 5:
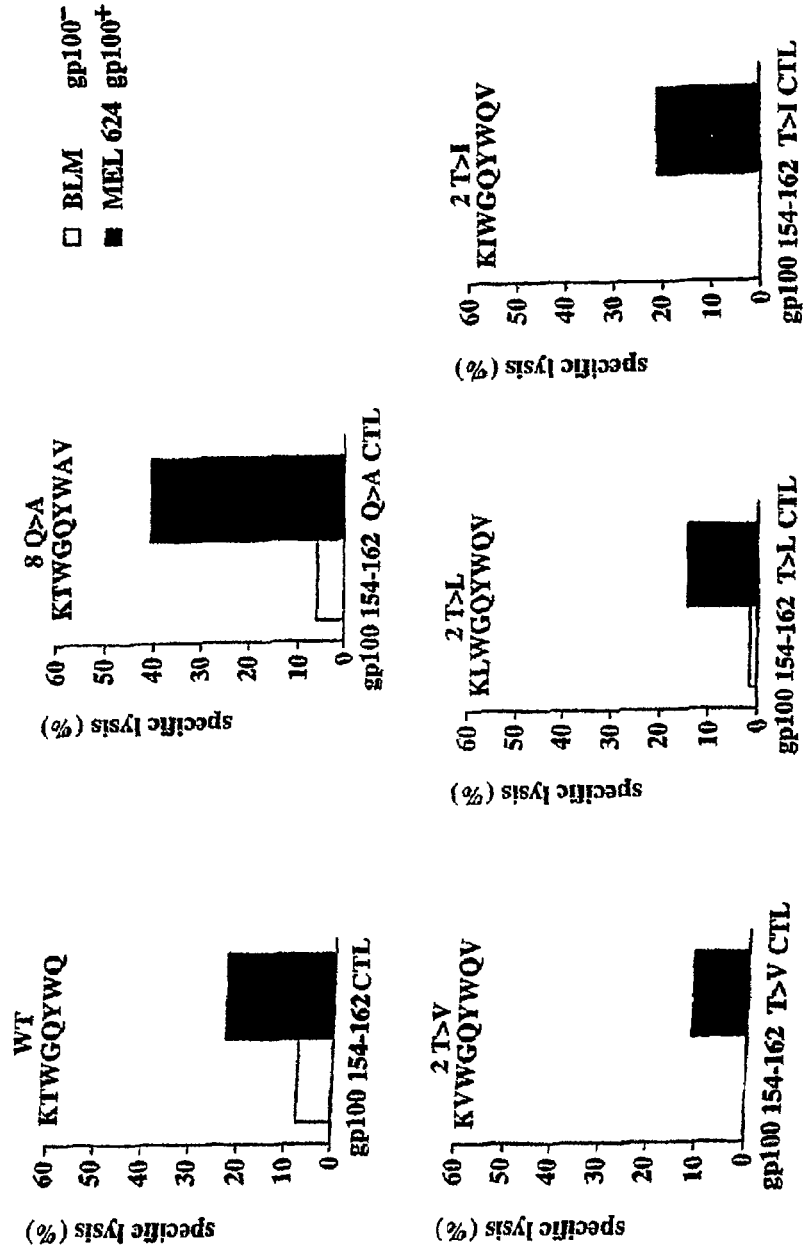
FIG. 5. KTWGQYWQV (SEQ ID NO: 9) and epitope-analogue KTWGQYWAV (SEQ ID NO: 1); KVWGQYWQV (SEQ ID NO: 2); KLWGQYWQV (SEQ ID NO: 3); and KIWGQYWQV (SEQ ID NO: 4) induced CTL cultures specifically lyse melanoma cells endogenously presenting the wild type epitope. Chromium-labeled HLA-A2.1$^+$ BLM and Mel 624 melanoma cells were used as target cells. BLM cells lack expression of gp100. The different CTL cultures were added at an effector to target ratio of 20:1. One representative experiment out of two is shown.

Next, we performed in vitro CTL induction assays to assess whether within the T cell repertoire of HLA-A*0201+ healthy donors precursor T lymphocytes were present capable of recognizing gp100 154-162 epitope-analogues. In order to achieve this, we initiated cultures of peptide-loaded dendritic cells together with autologous responder T lymphocytes as described previously (Bakker et al., 1995, *Cancer Res.* 55:5330). After several rounds of restimulation, responder T cells were tested for cytotoxic activity (FIG. 4). All bulk CTL populations raised against the gp100 154-162 epitope-analogues, KTWGQYWAV (SEQ ID NO: 1), KVWGQYWQV (SEQ ID NO: 2), KLWGQYWQV (SEQ ID NO: 3) and KIWGQYWQV (SEQ ID NO: 4), efficiently lysed HLA-A*0201+ T2 target cells incubated with the peptides used for CTL induction. Only low background lysis was observed in the presence of an irrelevant peptide. In addition, these gp100 154-162 epitope-analogue reactive CTL efficiently lysed T2 target cells incubated with wild type gp100 154-162. To address the question whether these CTL responder populations could also recognize endogenously processed and presented wild type epitope, we performed chromium-release experiments using HLA-A*0201+ melanoma cell lines BLM and Mel 624 as targets. BLM cells have lost expression of the gp100 antigen, both at the protein and at the mRNA level (Adema et al., 1993, *Am. J. Pathol.* 143:1579). As shown in FIG. 5, all peptide-induced CTL cultures lysed the antigen expressing Mel 624 cells, whereas no or background lysis was observed against antigen negative BLM cells. TNF release by the anti-gp100 154-162 analogue CTL further demonstrated the reactivity of these CTL with endogenously presented wild type gp100 154-162 (data not shown). These data show that the four different CTL cultures induced using gp100 154-162 epitope-analogue loaded dendritic cells, all recognized the native gp100 154-162 epitope endogenously processed and presented by HLA-A*0201+ Mel 624 cells.

TABLE I

HLA-A*0201-binding and target cell sensitization of alanine-replacement epitopes.

| Melan A/MART-1 27-35 | HLA-A*0201 stabilization[a] 50 µM | HLA-A*0201 stabilization[a] 25 µM | target cell lysis by TIL 1235[b] | gp100 154-162 | HLA-A*0201 stabilization 50 µM | HLA-A*0201 stabilization 25 µM | target cell lysis by TIL 1200 |
|---|---|---|---|---|---|---|---|
| YLEPGPVTA[c] (SEQ ID NO: 7) | 2.26 | 2.12 | −3 | YLEPGPVTA (SEQ ID NO: 7) | | | 3 |
| AAGIGILTV (SEQ ID NO: 8) | 1.20 | 1.11 | 40 | KTWGQYWQV (SEQ ID NO: 6) | 2.06 | 1.40 | 67 |
| GAGIGILTV (SEQ ID NO: 10) | 1.07 | 1.11 | 52 | ATWGQYWQV (SEQ ID NO: 11) | 1.94 | 1.42 | 75 |
| AGGIGILTV (SEQ ID NO: 12) | 0.96 | 1.05 | 6 | KAWGQYWQV (SEQ ID NO: 13) | 1.57 | 1.20 | 64 |
| AAAIGILTV (SEQ ID NO: 14) | 0.98 | 0.99 | 13 | KTAGQYWQV (SEQ ID NO: 15) | 1.17 | 1.02 | 58 |
| AAGAGILTV (SEQ ID NO: 16) | 0.93 | 0.97 | 0 | KTWAQYWQV (SEQ ID NO: 17) | 1.45 | 1.13 | 63 |
| AAGIAILTV (SEQ ID NO: 18) | 1.01 | 1.01 | 4 | KTWGAYWQV (SEQ ID NO: 19) | 1.59 | 1.25 | 9 |
| AAGIGALTV (SEQ ID NO: 20) | 0.93 | 1.00 | 2 | KTWGQAWQV (SEQ ID NO: 21) | 1.42 | 1.15 | 7 |
| AAGIGIATV (SEQ ID NO: 22) | 1.10 | 1.13 | 6 | KTWGQYAQV (SEQ ID NO: 23) | 1.31 | 1.14 | −2 |
| AAGIGILAV (SEQ ID NO: 24) | 1.05 | 1.01 | 11 | KTWGQYWAV (SEQ ID NO: 1) | 1.72 | 1.35 | 73 |
| AAGIGILTA (SEQ ID NO: 25) | 1.00 | 1.03 | 26 | KTWGQYWQA (SEQ ID NO: 26) | 1.08 | 1.02 | 76 |

[a]Binding of peptides to HLA-A2.1 was analyzed using the processing-defective T2 cell line at the indicated peptide concentrations. Numbers indicate Fluorescence Index: experimental mean fluorescence divided by the mean fluorescence that is obtained when T2 cells are incubated with an HLA-A2.1 non-binding peptide at a similar concentration.
[b]Numbers indicate % specific lysis by the relevant TIL lines at an E:T ratio of 20:1. Chromium-labeled T2 target cells were preincubated for 90 min with 1 µM of peptide. Chromium release was measured after 5 hours of incubation.
[c]gp100 280-288.

TABLE II

HLA-A*0201-binding and target cell sensitization of N-terminal anchor-replacement epitopes.

| Melan A/MART-1 27-35 | HLA-A*0201 stabilization[a] 50 µM | HLA-A*0201 stabilization[a] 25 µM | target cell lysis by TIL 1235[b] | gp100 154-162 | HLA-A*0201 stabilization 50 µM | HLA-A*0201 stabilization 25 µM | target cell lysis by TIL 1200 |
|---|---|---|---|---|---|---|---|
| YLEPGPVTA[c] (SEQ ID NO: 7) | 2.26 | 2.12 | −1 | YLEPGPVTA (SEQ ID NO: 7) | | | 3 |
| AAGIGILTV (SEQ ID NO: 8) | 1.20 | 1.11 | 40 | KTWGQYWQV (SEQ ID NO: 9) | 2.06 | 1.40 | 67 |
| AVGIGILTV (SEQ ID NO: 27) | 1.62 | 1.36 | 27 | KVWGQYWQV (SEQ ID NO: 2) | 2.13 | 1.57 | 69 |
| ALGIGILTV (SEQ ID NO: 28) | 2.21 | 1.93 | 16 | KLWGQYWQV (SEQ ID NO: 3) | 2.19 | 1.55 | 65 |
| AMGIGILTV (SEQ ID NO: 29) | 1.18 | 1.05 | 6 | KMWGQYWQV (SEQ ID NO: 35) | 1.73 | 1.28 | 57 |
| AIGIGILTV (SEQ ID NO: 30) | 1.58 | 1.29 | 27 | KIWGQYWQV (SEQ ID NO: 4) | 2.00 | 1.43 | 68 |

[a]Binding of peptides to HLA-A2.1 was analyzed using the processing-defective T2 cell line at the indicated peptide concentrations. Numbers indicate Fluorescence Index: experimental mean fluorescence divided by the mean fluorescence that is obtained when T2 cells are incubated with an HLA-A2.1 non-binding peptide at a similar concentration.
[b]Numbers indicate % specific lysis by the relevant TIL lines at an E:T ratio of 20:1. Chromium-labeled T2 target cells were preincubated for 90 min with 1 µM of peptide. Chromium release was measured after 5 hours of incubation.
[c]gp100 280-288.

TABLE III

HLA-A*0201 binding and complex stability of gp100 154-162 epitope-analogues

| peptide | | Affinity IC50 (µM)[a] | Stability (DT 50%)[b] |
|---|---|---|---|
| FLPSDFFPSV[c] | (SEQ ID NO: 31) | 0.5 | >4 hr |
| KTWGQYWQV | (SEQ ID NO: 9) | 1.4 | >4 hr |
| KTWGQYWAV | (SEQ ID NO: 1) | 0.5 | >4 hr |
| KVWGQYWQV | (SEQ ID NO: 2) | 0.8 | >4 hr |
| KLWGQYWQV | (SEQ ID NO: 3) | 0.4 | >4 hr |
| KIWGQYWQV | (SEQ ID NO: 4) | 0.6 | >4 hr |

[a]Binding of peptides to HLA-A*0201 was analyzed in a competition away at 4° C. using mild acid treated HLA-A*0201+B-LCL. The binding capacity of the peptides is shown as the concentration of peptide needed to inhibit 50% of binding of the Fluorescein labeled reference peptide.
[b]The dissociation rate of HLA-A*0201-peptide complexes was measured using emetine pretreated HLA-A*0201+B-LCL. After mild acid treatment, empty cell surface HLA-A*0201 molecules were loaded with peptide at room temperature and B-LCL were then put at 37° C. The decay of cell surface HLA-A*0201 molecules was analyzed by flow cytometry. The dissociation rate is depicted as the time required for 50% of the MHC class I-peptide complexes to decay at 37° C.
[c]HBC 18-27, unlabeled reference peptide.

What is claimed is:

1. A gp100 peptide consisting of SEQ ID NO: 1.

2. A pharmaceutical composition comprising the gp100 peptide of claim 1.

3. A method of eliciting a T-cell response in a mammal comprising administering to the mammal the peptide of claim 1 in an amount sufficient to elicit a T-cell response in the mammal.

* * * * *

SEQUENCE LISTING

<160> NUMBER OF SEQ ID NOS: 35

<210> SEQ ID NO 1
<211> LENGTH: 9
<212> TYPE: PRT
<213> ORGANISM: Artificial Sequence
<220> FEATURE:
<223> OTHER INFORMATION: Synthetic

<400> SEQUENCE: 1

Lys Thr Trp Gly Gln Tyr Trp Ala Val
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Lys Val Trp Gly Gln Tyr Trp Gln Val
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Lys Leu Trp Gly Gln Tyr Trp Gln Val
1               5

<210> SEQ ID NO 4
<211> LENGTH: 9
<212> TYPE: PRT
<213> ORGANISM: Artificial Sequence
<220> FEATURE:
<223> OTHER INFORMATION: Synthetic

<400> SEQUENCE: 4

```
Lys Ile Trp Gly Gln Tyr Trp Gln Val
1               5

<210> SEQ ID NO 5
<211> LENGTH: 13
<212> TYPE: PRT
<213> ORGANISM: Hepatitis B virus

<400> SEQUENCE: 5

Thr Pro Pro Ala Tyr Arg Pro Pro Asn Ala Pro Ile Leu
1               5                   10

<210> SEQ ID NO 6
<211> LENGTH: 10
<212> TYPE: PRT
<213> ORGANISM: Hepatitis B virus

<400> SEQUENCE: 6

Phe Leu Pro Ser Asp Asp Phe Pro Ser Val
1               5                   10

<210> SEQ ID NO 7
<211> LENGTH: 9
<212> TYPE: PRT
<213> ORGANISM: Homo sapiens

<400> SEQUENCE: 7

Tyr Leu Glu Pro Gly Pro Val Thr Ala
1               5

<210> SEQ ID NO 8
<211> LENGTH: 9
<212> TYPE: PRT
<213> ORGANISM: Homo sapiens

<400> SEQUENCE: 8

Ala Ala Gly Ile Gly Ile Leu Thr Val
1               5

<210> SEQ ID NO 9
<211> LENGTH: 9
<212> TYPE: PRT
<213> ORGANISM: Homo sapiens

<400> SEQUENCE: 9

Lys Thr Trp Gly Gln Tyr Trp Gln Val
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Gly Ala Gly Ile Gly Ile Leu Thr Val
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 11

Ala Thr Trp Gly Gln Tyr Trp Gln Val
1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic

<400> SEQUENCE: 12

Ala Gly Gly Ile Gly Ile Leu Thr Val
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Lys Ala Trp Gly Gln Tyr Trp Gln Val
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic

<400> SEQUENCE: 14

Ala Ala Ala Ile Gly Ile Leu Thr Val
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic

<400> SEQUENCE: 15

Lys Thr Ala Gly Gln Tyr Trp Gln Val
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Ala Ala Gly Ala Gly Ile Leu Thr Val
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic
```

```
<400> SEQUENCE: 17

Lys Thr Trp Ala Gln Tyr Trp Gln Val
1               5

<210> SEQ ID NO 18
<211> LENGTH: 9
<212> TYPE: PRT
<213> ORGANISM: Artificial Sequence
<220> FEATURE:
<223> OTHER INFORMATION: Synthetic

<400> SEQUENCE: 18

Ala Ala Gly Ile Ala Ile Leu Thr Val
1               5

<210> SEQ ID NO 19
<211> LENGTH: 9
<212> TYPE: PRT
<213> ORGANISM: Artificial Sequence
<220> FEATURE:
<223> OTHER INFORMATION: Synthetic

<400> SEQUENCE: 19

Lys Thr Trp Gly Ala Tyr Trp Gln Val
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic

<400> SEQUENCE: 20

Ala Ala Gly Ile Gly Ala Leu Thr Val
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Lys Thr Trp Gly Gln Ala Trp Gln Val
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic

<400> SEQUENCE: 22

Ala Ala Gly Ile Gly Ile Ala Thr Val
1               5

<210> SEQ ID NO 23
<211> LENGTH: 9
<212> TYPE: PRT
<213> ORGANISM: Artificial Sequence
<220> FEATURE:
<223> OTHER INFORMATION: Synthetic

<400> SEQUENCE: 23
```

```
Lys Thr Trp Gly Gln Tyr Ala Gln Val
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Ala Ala Gly Ile Gly Ile Leu Ala Val
1               5

<210> SEQ ID NO 25
<211> LENGTH: 9
<212> TYPE: PRT
<213> ORGANISM: Artificial Sequence
<220> FEATURE:
<223> OTHER INFORMATION: Synthetic

<400> SEQUENCE: 25

Ala Ala Gly Ile Gly Ile Leu Thr Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic

<400> SEQUENCE: 26

Lys Thr Trp Gly Gln Tyr Trp Gln Ala
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic

<400> SEQUENCE: 27

Ala Val Gly Ile Gly Ile Leu Thr Val
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic

<400> SEQUENCE: 28

Ala Leu Gly Ile Gly Ile Leu Thr Val
1               5

<210> SEQ ID NO 29
<211> LENGTH: 9
<212> TYPE: PRT
<213> ORGANISM: Artificial Sequence
<220> FEATURE:
<223> OTHER INFORMATION: Synthetic

<400> SEQUENCE: 29
```

```
Ala Met Gly Ile Gly Ile Leu Thr Val
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic

<400> SEQUENCE: 30

Ala Ile Gly Ile Gly Leu Thr Val
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Phe Leu Pro Ser Asp Phe Phe Pro Ser Val
1               5                   10

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Lys Ile Trp Gly Gln Tyr Trp Ala Val
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic

<400> SEQUENCE: 33

Lys Leu Trp Gly Gln Tyr Trp Ala Val
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic

<400> SEQUENCE: 34

Lys Val Trp Gly Gln Tyr Trp Ala Val
1               5

<210> SEQ ID NO 35
<211> LENGTH: 9
<212> TYPE: PRT
<213> ORGANISM: Artificial Sequence
```

-continued

```
<220> FEATURE:
<223> OTHER INFORMATION: Synthetic

<400> SEQUENCE: 35

Lys Met Trp Gly Gln Tyr Trp Gln Val
1               5
```